(12) United States Patent
Werneth et al.

(10) Patent No.: US 10,828,011 B2
(45) Date of Patent: Nov. 10, 2020

(54) DEVICES AND METHODS FOR DETERMINATION OF ELECTRICAL DIPOLE DENSITIES ON A CARDIAC SURFACE

(71) Applicant: Acutus Medical, Inc., Carlsbad, CA (US)

(72) Inventors: Randell L. Werneth, Boise, ID (US); Graydon E. Beatty, Bloomington, MN (US); Christoph Scharf, Horgen (CH); Gunter Scharf, Zurich (CH); J. Christopher Flaherty, Auburndale, FL (US)

(73) Assignee: ACUTUS MEDICAL, INC., Carlsbad, CA (US)

( * ) Notice: Subject to any disclaimer, the term of this patent is extended or adjusted under 35 U.S.C. 154(b) by 0 days.

(21) Appl. No.: 14/916,056

(22) PCT Filed: Sep. 10, 2014

(86) PCT No.: PCT/US2014/054942
§ 371 (c)(1),
(2) Date: Mar. 2, 2016

(87) PCT Pub. No.: WO2015/038607
PCT Pub. Date: Mar. 19, 2015

(65) Prior Publication Data
US 2016/0192902 A1 Jul. 7, 2016

Related U.S. Application Data

(60) Provisional application No. 61/877,617, filed on Sep. 13, 2013.

(51) Int. Cl.
*A61B 5/00* (2006.01)
*A61B 5/0452* (2006.01)
(Continued)

(52) U.S. Cl.
CPC ............ *A61B 8/4416* (2013.01); *A61B 3/113* (2013.01); *A61B 5/0036* (2018.08);
(Continued)

(58) Field of Classification Search
CPC ....... A61B 8/4416; A61B 8/0883; A61B 8/14; A61B 8/08; A61B 8/0858; A61B 5/04012;
(Continued)

(56) References Cited

U.S. PATENT DOCUMENTS

| | | | |
|---|---|---|---|
| 4,173,228 A | 11/1979 | Van Steenwyk et al. | |
| 5,041,973 A | 8/1991 | Lebron et al. | |

(Continued)

FOREIGN PATENT DOCUMENTS

| | | |
|---|---|---|
| CA | 2829626 | 9/2012 |
| CN | 1856123 | 11/2006 |

(Continued)

OTHER PUBLICATIONS

International Search Report dated Mar. 10, 2015 issued in corresponding International Application No. PCT/US14/54942.

(Continued)

*Primary Examiner* — Mallika D Firchild
*Assistant Examiner* — Nathan A Baldwin
(74) *Attorney, Agent, or Firm* — Onello & Mello, LLP

(57) ABSTRACT

Disclosed are devices, systems, and methods for determining the dipole densities on a cardiac surface using electrodes positioned on a torso of a patient. Electrodes are integrated into a piece of clothing worn by a patient. The clothing serves to fix the position of the electrodes adjacent a patient's torso. Ultrasonic transducers and sensors are used to determine a distance between the epicardial surface and (Continued)

the electrodes and are also used to detect epicardial surface motion as well as epicardial wall thickness.

45 Claims, 4 Drawing Sheets

(51) Int. Cl.
| | |
|---|---|
| A61B 8/00 | (2006.01) |
| A61B 8/08 | (2006.01) |
| A61B 5/0408 | (2006.01) |
| A61B 5/107 | (2006.01) |
| A61B 3/113 | (2006.01) |
| A61B 5/0205 | (2006.01) |
| A61B 5/04 | (2006.01) |
| A61B 5/042 | (2006.01) |
| A61B 5/0432 | (2006.01) |
| A61B 5/044 | (2006.01) |
| A61B 5/0478 | (2006.01) |
| A61B 6/03 | (2006.01) |
| A61B 8/12 | (2006.01) |
| A61B 18/02 | (2006.01) |
| A61B 18/14 | (2006.01) |
| A61B 18/18 | (2006.01) |
| A61B 18/20 | (2006.01) |
| A61B 18/00 | (2006.01) |

(52) U.S. Cl.
CPC ............ *A61B 5/0205* (2013.01); *A61B 5/044* (2013.01); *A61B 5/04012* (2013.01); *A61B 5/0422* (2013.01); *A61B 5/0432* (2013.01); *A61B 5/0452* (2013.01); *A61B 5/0478* (2013.01); *A61B 5/04085* (2013.01); *A61B 5/1072* (2013.01); *A61B 5/4836* (2013.01); *A61B 5/6805* (2013.01); *A61B 6/032* (2013.01); *A61B 8/0883* (2013.01); *A61B 8/12* (2013.01); *A61B 8/464* (2013.01); *A61B 8/565* (2013.01); *A61B 18/02* (2013.01); *A61B 18/1492* (2013.01); *A61B 18/1815* (2013.01); *A61B 18/20* (2013.01); *A61B 2018/00994* (2013.01); *A61B 2562/046* (2013.01); *A61B 2576/023* (2013.01)

(58) Field of Classification Search
CPC ............... A61B 5/0408; A61B 5/04085; A61B 5/04011; A61B 5/0432; A61B 5/0452; A61B 5/6805; A61B 5/6804; A61B 5/6802; A61B 5/6801; A61B 5/6823
See application file for complete search history.

(56) References Cited

U.S. PATENT DOCUMENTS

| | | | |
|---|---|---|---|
| 5,156,151 A | 10/1992 | Imran | |
| 5,293,868 A | 3/1994 | Nardella | |
| 5,482,472 A | 1/1996 | Garoni et al. | |
| 5,499,981 A | 3/1996 | Kordis | |
| 5,555,883 A | 9/1996 | Avitall | |
| 5,595,183 A | 1/1997 | Swanson et al. | |
| 5,601,084 A | 2/1997 | Sheehan et al. | |
| 5,647,367 A | 7/1997 | Lum et al. | |
| 5,662,108 A | 9/1997 | Budd et al. | |
| 5,722,402 A | 3/1998 | Swanson et al. | |
| 5,722,416 A | 3/1998 | Swanson et al. | |
| 5,740,808 A | 4/1998 | Panescu et al. | |
| 5,749,833 A | 5/1998 | Hakki et al. | |
| 5,759,158 A | 6/1998 | Swanson | |
| 5,782,239 A | 7/1998 | Webster, Jr. | |
| 5,795,298 A | 8/1998 | Vesely et al. | |
| 5,795,299 A | 8/1998 | Eaton et al. | |
| 5,820,568 A | 10/1998 | Parker | |
| 5,830,144 A | 11/1998 | Vesely | |
| 5,846,198 A | 12/1998 | Killmann | |
| 5,876,336 A | 3/1999 | Swanson et al. | |
| 5,928,228 A | 7/1999 | Kordis et al. | |
| 5,944,022 A | 8/1999 | Nardella et al. | |
| 5,968,040 A | 10/1999 | Swanson et al. | |
| 6,014,590 A | 1/2000 | Whayne et al. | |
| 6,024,703 A | 2/2000 | Zanelli et al. | |
| 6,066,096 A | 5/2000 | Smith et al. | |
| 6,086,532 A | 7/2000 | Panescu et al. | |
| 6,107,699 A | 8/2000 | Swanson | |
| 6,115,626 A | 9/2000 | Whayne et al. | |
| 6,187,032 B1 | 2/2001 | Ohyu et al. | |
| 6,188,928 B1 | 2/2001 | Noren et al. | |
| 6,216,027 B1 | 4/2001 | Willis et al. | |
| 6,216,043 B1 | 4/2001 | Swanson et al. | |
| 6,240,307 B1 | 5/2001 | Beatty et al. | |
| 6,301,496 B1 | 10/2001 | Reisfeld | |
| 6,396,198 B1 | 5/2002 | Okimura et al. | |
| 6,400,981 B1 | 6/2002 | Govari | |
| 6,490,474 B1 | 12/2002 | Willis et al. | |
| 6,514,249 B1 | 2/2003 | Maguire et al. | |
| 6,574,492 B1 | 6/2003 | Ben-Haim et al. | |
| 6,640,119 B1 | 10/2003 | Budd et al. | |
| 6,716,166 B2 | 4/2004 | Govari | |
| 6,728,562 B1 | 4/2004 | Budd et al. | |
| 6,773,402 B2 | 8/2004 | Govari et al. | |
| 6,824,515 B2 | 11/2004 | Suorsa et al. | |
| 6,826,420 B1 | 11/2004 | Beatty et al. | |
| 6,826,421 B1 | 11/2004 | Beatty et al. | |
| 6,839,588 B1 | 1/2005 | Rudy | |
| 6,939,309 B1 | 9/2005 | Beatty et al. | |
| 6,950,689 B1 | 9/2005 | Willis et al. | |
| 6,970,733 B2 | 11/2005 | Willis et al. | |
| 6,978,168 B2 | 12/2005 | Beatty et al. | |
| 6,990,370 B1 | 1/2006 | Beatty et al. | |
| 7,187,964 B2 | 3/2007 | Khoury | |
| 7,187,973 B2 | 3/2007 | Hauck | |
| 7,258,674 B2 | 8/2007 | Hillstead et al. | |
| 7,285,119 B2 | 10/2007 | Stewart et al. | |
| 7,289,843 B2 | 10/2007 | Beatty et al. | |
| 7,291,146 B2 | 11/2007 | Steinke et al. | |
| 7,351,914 B2 | 4/2008 | Kaneto et al. | |
| 7,505,810 B2 | 3/2009 | Harlev et al. | |
| 7,573,182 B2 | 8/2009 | Savage | |
| 7,766,838 B2 | 8/2010 | Yagi et al. | |
| 7,841,986 B2 | 11/2010 | He et al. | |
| 7,918,793 B2 | 4/2011 | Altmann et al. | |
| 7,953,475 B2 | 5/2011 | Harlev et al. | |
| 8,103,327 B2 | 1/2012 | Harlev et al. | |
| 8,147,486 B2 | 4/2012 | Honour et al. | |
| 8,150,499 B2 | 4/2012 | Gelbart et al. | |
| 8,175,680 B2 | 5/2012 | Panescu | |
| 8,208,998 B2 | 6/2012 | Beatty et al. | |
| 8,221,411 B2 | 7/2012 | Francischelli et al. | |
| 8,233,972 B2 | 7/2012 | Zhang | |
| 8,320,711 B2 | 11/2012 | Altmann et al. | |
| 8,346,339 B2 | 1/2013 | Kordis et al. | |
| 8,360,786 B2 | 1/2013 | Duryea | |
| 8,364,234 B2 | 1/2013 | Kordis et al. | |
| 8,412,307 B2 | 4/2013 | Willis et al. | |
| 8,417,313 B2 | 4/2013 | Scharf et al. | |
| 8,428,690 B2 | 4/2013 | Li et al. | |
| 8,447,377 B2 | 5/2013 | Harlev et al. | |
| 8,454,596 B2 | 6/2013 | Ma et al. | |
| 8,478,388 B2 | 7/2013 | Nguyen et al. | |
| 8,512,255 B2 | 8/2013 | Scharf et al. | |
| 8,571,647 B2 | 10/2013 | Harlev et al. | |
| 8,700,119 B2 | 4/2014 | Scharf et al. | |
| 8,755,861 B2 | 6/2014 | Harlev et al. | |
| 8,825,130 B2 | 9/2014 | Just et al. | |
| 8,825,134 B2 | 9/2014 | Danehorn | |
| 8,918,158 B2 | 12/2014 | Scharf et al. | |
| 8,934,988 B2 | 1/2015 | Persson et al. | |
| 8,948,837 B2 | 2/2015 | Harlev et al. | |
| 8,968,299 B2 | 3/2015 | Kauphusman et al. | |
| 8,979,839 B2 | 3/2015 | De La Rama et al. | |
| 8,989,842 B2 | 3/2015 | Li et al. | |

(56) References Cited

U.S. PATENT DOCUMENTS

| | | |
|---|---|---|
| 9,011,423 B2 | 4/2015 | Brewster et al. |
| 9,026,196 B2 | 5/2015 | Curran et al. |
| 9,037,259 B2 | 5/2015 | Mathur |
| 9,044,245 B2 | 6/2015 | Condie et al. |
| 9,167,982 B2 | 10/2015 | Scharf et al. |
| 9,186,081 B2 | 11/2015 | Afonso et al. |
| 9,186,212 B2 | 11/2015 | Nabutovsky et al. |
| 9,192,318 B2 | 11/2015 | Scharf et al. |
| 9,220,432 B2 | 12/2015 | Bukhman |
| 9,241,687 B2 | 1/2016 | Mcgee |
| 9,351,789 B2 | 5/2016 | Novichenok et al. |
| D758,596 S | 6/2016 | Perryman et al. |
| 9,358,398 B2 | 6/2016 | Moffitt et al. |
| 9,474,486 B2 | 10/2016 | Eliason et al. |
| 9,480,525 B2 | 11/2016 | Lopes et al. |
| 9,486,355 B2 | 11/2016 | Gustus et al. |
| 9,492,227 B2 | 11/2016 | Lopes et al. |
| 9,492,228 B2 | 11/2016 | Lopes et al. |
| 9,498,192 B2 | 11/2016 | Hashimshony et al. |
| 9,504,395 B2 | 11/2016 | Scharf et al. |
| 9,526,573 B2 | 12/2016 | Lopes et al. |
| 9,549,708 B2 | 1/2017 | Mercanzini et al. |
| 9,579,149 B2 | 2/2017 | Kelly et al. |
| 9,585,588 B2 | 3/2017 | Marecki et al. |
| 9,610,024 B2 | 4/2017 | Scharf et al. |
| 9,713,730 B2 | 7/2017 | Mathur et al. |
| 9,717,555 B2 | 8/2017 | Chan et al. |
| 9,717,559 B2 | 8/2017 | Ditter et al. |
| 9,730,602 B2 | 8/2017 | Harlev et al. |
| 9,757,044 B2 | 9/2017 | Scharf et al. |
| 9,827,039 B2 | 11/2017 | Dandler et al. |
| 10,004,459 B2 | 6/2018 | Werneth et al. |
| 10,028,706 B2 | 7/2018 | Brockway et al. |
| 10,082,395 B2 | 9/2018 | Koyrakh et al. |
| 10,201,311 B2 | 2/2019 | Chou et al. |
| 10,405,828 B2 | 9/2019 | Deladi et al. |
| 2001/0007070 A1 | 7/2001 | Stewart et al. |
| 2002/0026118 A1 | 2/2002 | Govari |
| 2002/0045810 A1 | 4/2002 | Ben-Hai |
| 2002/0128565 A1* | 9/2002 | Rudy ............... A61B 5/0422 600/509 |
| 2002/0165441 A1 | 11/2002 | Coleman et al. |
| 2003/0036696 A1 | 2/2003 | Willis et al. |
| 2003/0065271 A1 | 4/2003 | Khoury |
| 2003/0120318 A1 | 6/2003 | Hauck |
| 2003/0153907 A1 | 8/2003 | Suorsa et al. |
| 2003/0158477 A1 | 8/2003 | Panescu |
| 2003/0176799 A1 | 9/2003 | Beatty et al. |
| 2003/0231789 A1 | 12/2003 | Willis et al. |
| 2003/0236466 A1* | 12/2003 | Tarjan ............... A61B 5/0408 600/508 |
| 2004/0039312 A1 | 2/2004 | Hillstead et al. |
| 2004/0082870 A1 | 4/2004 | Rudy et al. |
| 2004/0082948 A1 | 4/2004 | Stewart et al. |
| 2004/0254437 A1 | 12/2004 | Hauck et al. |
| 2005/0059880 A1 | 3/2005 | Mathias et al. |
| 2005/0101874 A1 | 5/2005 | Beatty et al. |
| 2005/0113665 A1 | 5/2005 | Mohr et al. |
| 2005/0148836 A1 | 7/2005 | Kleen et al. |
| 2005/0203375 A1 | 9/2005 | Willis et al. |
| 2006/0052716 A1 | 3/2006 | Beatty et al. |
| 2006/0058663 A1 | 3/2006 | Willis et al. |
| 2006/0058676 A1 | 3/2006 | Yagi et al. |
| 2006/0058692 A1 | 3/2006 | Beatty et al. |
| 2006/0058693 A1 | 3/2006 | Beatty et al. |
| 2006/0084884 A1 | 4/2006 | Beatty et al. |
| 2006/0084970 A1 | 4/2006 | Beatty et al. |
| 2006/0084971 A1 | 4/2006 | Beatty et al. |
| 2006/0084972 A1 | 4/2006 | Beatty et al. |
| 2006/0116576 A1 | 6/2006 | McGee et al. |
| 2006/0244177 A1 | 11/2006 | Kaneto et al. |
| 2007/0055150 A1 | 3/2007 | Donaldson et al. |
| 2007/0060832 A1 | 3/2007 | Levin |
| 2007/0083194 A1 | 4/2007 | Kunis et al. |
| 2007/0106146 A1 | 5/2007 | Altmann et al. |
| 2007/0177770 A1* | 8/2007 | Derchak ............ G06K 9/00496 382/115 |
| 2007/0232949 A1 | 10/2007 | Saksena |
| 2008/0009758 A1 | 1/2008 | Voth |
| 2008/0146937 A1 | 6/2008 | Lee et al. |
| 2008/0287777 A1 | 11/2008 | Li et al. |
| 2008/0319297 A1* | 12/2008 | Danehorn ............ A61M 25/01 600/373 |
| 2009/0024086 A1 | 1/2009 | Zhang et al. |
| 2009/0076483 A1 | 3/2009 | Danehorn |
| 2009/0082691 A1 | 3/2009 | Denison et al. |
| 2009/0131930 A1 | 5/2009 | Gelbart et al. |
| 2009/0143651 A1 | 6/2009 | Kallback et al. |
| 2009/0148012 A1 | 6/2009 | Altmann et al. |
| 2009/0171274 A1 | 7/2009 | Harlev et al. |
| 2009/0264781 A1 | 10/2009 | Scharf |
| 2010/0023004 A1 | 1/2010 | Francischelli et al. |
| 2010/0076426 A1 | 3/2010 | de la Rama et al. |
| 2010/0094279 A1 | 4/2010 | Kauphusman et al. |
| 2010/0168578 A1* | 7/2010 | Garson, Jr. .......... A61B 8/0858 600/443 |
| 2010/0256627 A1 | 10/2010 | Ma et al. |
| 2010/0279263 A1 | 11/2010 | Duryea |
| 2010/0286551 A1 | 11/2010 | Harlev et al. |
| 2010/0298690 A1* | 11/2010 | Scharf ................. A61B 5/0422 600/407 |
| 2011/0045130 A1 | 2/2011 | Edens et al. |
| 2011/0077526 A1* | 3/2011 | Zwirn ................. A61B 5/0095 600/459 |
| 2011/0092809 A1 | 4/2011 | Nguyen et al. |
| 2011/0118726 A1 | 5/2011 | De La Rama et al. |
| 2011/0125172 A1 | 5/2011 | Gelbart et al. |
| 2011/0144510 A1 | 6/2011 | Ryu et al. |
| 2011/0172658 A1 | 7/2011 | Gelbart et al. |
| 2011/0201951 A1 | 8/2011 | Zhang |
| 2011/0213231 A1 | 9/2011 | Hall et al. |
| 2011/0270237 A1 | 11/2011 | Werneth et al. |
| 2012/0078077 A1 | 3/2012 | Harlev et al. |
| 2012/0082969 A1 | 4/2012 | Schwartz et al. |
| 2012/0123296 A1 | 5/2012 | Hashimshony et al. |
| 2012/0136231 A1 | 5/2012 | Markel |
| 2012/0143298 A1 | 6/2012 | Just et al. |
| 2012/0165667 A1 | 6/2012 | Altmann et al. |
| 2012/0172859 A1 | 7/2012 | Condie et al. |
| 2012/0184863 A1 | 7/2012 | Harlev et al. |
| 2012/0271138 A1 | 10/2012 | Kordis et al. |
| 2012/0271139 A1 | 10/2012 | Kordis et al. |
| 2012/0277574 A1 | 11/2012 | Panescu |
| 2012/0302912 A1 | 11/2012 | Moffitt et al. |
| 2012/0310064 A1 | 12/2012 | Mcgee |
| 2013/0006238 A1 | 1/2013 | Ditter et al. |
| 2013/0085361 A1 | 4/2013 | Mercanzini et al. |
| 2013/0096432 A1 | 4/2013 | Hauck |
| 2013/0158537 A1* | 6/2013 | Deladi ............... A61B 18/1492 606/33 |
| 2013/0165916 A1 | 6/2013 | Mathur |
| 2013/0172715 A1 | 7/2013 | Just et al. |
| 2013/0178851 A1 | 7/2013 | Lopes et al. |
| 2013/0190587 A1 | 7/2013 | Lopes et al. |
| 2013/0197614 A1 | 8/2013 | Gustus et al. |
| 2013/0225983 A1 | 8/2013 | Willis et al. |
| 2013/0226017 A1 | 8/2013 | Scharf et al. |
| 2013/0241929 A1 | 9/2013 | Massarwa et al. |
| 2013/0245433 A1 | 9/2013 | Deladi et al. |
| 2013/0245621 A1 | 9/2013 | Persson et al. |
| 2013/0253298 A1 | 9/2013 | Harlev et al. |
| 2013/0267853 A1 | 10/2013 | Dausch et al. |
| 2013/0274582 A1 | 10/2013 | Afonso et al. |
| 2013/0282084 A1 | 10/2013 | Mathur et al. |
| 2013/0304062 A1 | 11/2013 | Chan et al. |
| 2013/0304065 A1 | 11/2013 | Lopes et al. |
| 2013/0310827 A1 | 11/2013 | Brewster et al. |
| 2013/0330701 A1 | 12/2013 | Rubinstein et al. |
| 2014/0024910 A1 | 1/2014 | Scharf et al. |
| 2014/0095105 A1 | 4/2014 | Koyrakh et al. |
| 2014/0121470 A1 | 5/2014 | Scharf et al. |
| 2014/0180150 A1 | 6/2014 | Scharf et al. |
| 2014/0249505 A1 | 9/2014 | Bukhman |
| 2014/0257069 A1 | 9/2014 | Eliason et al. |

(56) References Cited

U.S. PATENT DOCUMENTS

| | | |
|---|---|---|
| 2014/0257071 A1 | 9/2014 | Curran et al. |
| 2014/0275921 A1 | 9/2014 | Harlev et al. |
| 2014/0276733 A1 | 9/2014 | VanScoy et al. |
| 2014/0276746 A1 | 9/2014 | Nabutovsky et al. |
| 2014/0276789 A1 | 9/2014 | Dandler et al. |
| 2014/0358143 A1 | 12/2014 | Novichenok et al. |
| 2015/0196217 A1 | 7/2015 | Harlev et al. |
| 2015/0196219 A1 | 7/2015 | Scharf et al. |
| 2015/0208938 A1 | 7/2015 | Houben et al. |
| 2015/0223757 A1 | 8/2015 | Werneth et al. |
| 2015/0257732 A1 | 9/2015 | Ryan |
| 2015/0257825 A1 | 9/2015 | Kelly et al. |
| 2015/0342491 A1 | 12/2015 | Marecki et al. |
| 2015/0366508 A1 | 12/2015 | Chou et al. |
| 2015/0374252 A1 | 12/2015 | de la Rama et al. |
| 2016/0007869 A1 | 1/2016 | Scharf et al. |
| 2016/0038051 A1 | 2/2016 | Scharf et al. |
| 2016/0051321 A1 | 2/2016 | Salahieh et al. |
| 2016/0100770 A1 | 4/2016 | Afonso et al. |
| 2016/0128771 A1 | 5/2016 | Ditter et al. |
| 2016/0128772 A1 | 5/2016 | Reinders et al. |
| 2016/0256112 A1 | 9/2016 | Brockway et al. |
| 2017/0035486 A1 | 2/2017 | Lopes et al. |
| 2017/0100049 A1 | 4/2017 | Scharf et al. |
| 2017/0311833 A1 | 11/2017 | Afonso et al. |
| 2017/0319180 A1 | 11/2017 | Henneken et al. |
| 2019/0159729 A1 | 5/2019 | Chou et al. |

FOREIGN PATENT DOCUMENTS

| | | |
|---|---|---|
| CN | 101048100 | 10/2007 |
| CN | 201223445 | 4/2009 |
| CN | 201275144 | 7/2009 |
| CN | 102770085 | 11/2012 |
| CN | 104462650 | 3/2015 |
| EP | 1166714 | 1/2002 |
| EP | 1760661 | 3/2007 |
| EP | 1779787 | 5/2007 |
| EP | 2051625 | 2/2008 |
| EP | 2051625 | 4/2009 |
| EP | 2252203 | 11/2010 |
| EP | 2683293 | 1/2014 |
| EP | 2953550 | 8/2016 |
| JP | 08501477 | 2/1996 |
| JP | 08504333 | 5/1996 |
| JP | 10137207 | 5/1998 |
| JP | 11504541 | 4/1999 |
| JP | 2000510030 | 8/2000 |
| JP | 2000510250 | 8/2000 |
| JP | 2000358299 | 12/2000 |
| JP | 2001070269 | 3/2001 |
| JP | 2001522288 | 11/2001 |
| JP | 2002051998 | 2/2002 |
| JP | 2002113004 | 4/2002 |
| JP | 2002522106 | 7/2002 |
| JP | 2003511098 | 3/2003 |
| JP | 2004350702 | 12/2004 |
| JP | 2005536313 | 12/2005 |
| JP | 2006511296 | 4/2006 |
| JP | 2008149132 | 7/2008 |
| JP | 2009135109 | 6/2009 |
| JP | 2009136679 | 6/2009 |
| JP | 2011504363 | 2/2011 |
| JP | 2011507656 | 3/2011 |
| JP | 2013188476 | 9/2013 |
| JP | 2014506171 | 3/2014 |
| JP | 2014514031 | 6/2014 |
| JP | 2014516723 | 7/2014 |
| JP | 2016511026 | 4/2016 |
| JP | 2017514553 | 6/2017 |
| WO | 1994006349 | 3/1994 |
| WO | 199905971 | 2/1999 |
| WO | 2000007501 | 2/2000 |
| WO | 2004026134 | 4/2001 |
| WO | 200245608 | 6/2002 |
| WO | 2002045608 | 6/2002 |
| WO | 2003026722 | 4/2003 |
| WO | 2004060158 | 7/2004 |
| WO | 2006060613 | 6/2006 |
| WO | 2008014629 | 2/2008 |
| WO | 2009065042 | 5/2009 |
| WO | 2009090547 | 7/2009 |
| WO | 2011136867 | 11/2011 |
| WO | 2012068471 | 5/2012 |
| WO | 2012092016 | 7/2012 |
| WO | 2012100184 | 7/2012 |
| WO | 2012100185 | 7/2012 |
| WO | 2012110942 | 8/2012 |
| WO | 2012122517 | 9/2012 |
| WO | 2013101257 | 7/2013 |
| WO | 2014036439 | 3/2014 |
| WO | 2014124231 | 8/2014 |
| WO | 2014130169 | 8/2014 |
| WO | 2014137897 | 9/2014 |
| WO | 2015148470 | 10/2015 |
| WO | 2016183285 | 11/2016 |
| WO | 2017192769 | 11/2017 |
| WO | 2017192775 | 11/2017 |

OTHER PUBLICATIONS

Canadian Office Action dated Jan. 22, 2018 issued in corresponding Canadian Application No. 2932956.
Japanese Notice of Allowance dated Feb. 22, 2018 issued in corresponding Japanese Application No. 2015-530101, with English translation.
Decision dated Jan. 18, 2018 issued for European Patent Application No. 13176658.6.
Decision dated Jan. 16, 2018 issued for European Patent Application No. 09702094.5.
Canadian Office Action dated Nov. 27, 2017 issued in corresponding Canadian Application No. 2829626.
Extended European Search Report dated Mar. 14, 2017 issued in corresponding European Application No. EP14843283.4.
Office Action dated Apr. 27, 2016 in corresponding Canadian Application No. 2,747,859.
Christoph Scharf, et al. Declaration under 37 C.F.R. 1.132, Nov. 15, 2012.
Canadian Office Action dated Apr. 26, 2017 issued in corresponding Canadian Application No. 2932956.
Canadian Office Action dated Mar. 30, 2017 issued in corresponding Canadian Application No. 2747859.
Chinese Office Action dated Apr. 17, 2017 issued in corresponding Chinese Application No. 201480018328.4.
European Office Action dated Apr. 28, 2014, issued in corresponding European Application No. 09 702 094.5-1660.
European Office Action dated Feb. 29, 2016 issued in corresponding European Application No. 07 785 075.8-1657.
European Office Action dated Mar. 21, 2017 issued in corresponding European Application No. 07785075.8.
Extended European Search Report dated Oct. 18, 2017, issued in European Application No. 15768711.
International Search Report and Written Opinion dated Jun. 26, 2015 issued in International Application No. PCT/US2015/022187.
International Search Report dated Jun. 5, 2014 issued in corresponding PCT application WO 20141036439.
International Search Report dated Sep. 10, 2014 issued in corresponding International Application No. PCT/US14/54942.
International Search Report issued Apr. 14, 2008 in related International Application No. PCT/CH2007/000380.
Invitation to Pay Additional Fees dated Jan. 8, 2014 in corresponding International Application No. PCT/US2013/057579.
ISRWO dated May 20, 2014 in International application No. PCT/US14/15261.
Japanese Office Action dated Jan. 31, 2017 issued in corresponding Japanese Application No. 2013-557-926, with English language summary.

(56) References Cited

OTHER PUBLICATIONS

Japanese Office Action dated Jun. 27, 2017 issued in corresponding Japanese Application No. 2015-530101, with English language translation.
Japanese Office Action dated Sep. 26, 2017 issued in corresponding Japanese Application No. 2017-155346, with English translation.
Office Action dated Nov. 7, 2017, issued in European Application No. 15768711.
Office Action dated Oct. 10, 2017, issued in Application No. 2015-557091 with machine translation to English.
Office Action dated Mar. 9, 2016 in corresponding European Patent Application No. 13176658.6.
Office Action dated May 30, 2016 in related Australian Patent Application No. 2012225250.
Office Action dated Oct. 4, 2013 in corresponding Canadian Patent Application No. 2,659,898.
PCT ISRWO dated Jun. 5, 2014, issued in corresponding PCT Application No. PCT/US2013/057579.
Examination report dated Jul. 6, 2017 issued in Australian Patent Application No. 2014214756.
Della Bella et al. "Non-contact mapping to guide catheter ablation of untolerated ventrical tachycardia" European Heart Journal, May 2002, 23(9)742-752.
Examiner's Report dated Dec. 22, 2015 in related Canadian Application No. 2656898.
Extended European Search Report for related Application No. 13176658 dated Sep. 29, 2014.
Extended European Search Report dated Jul. 8, 2016 in related European Application No. 14748567.6.
Gupta et al. "Point of view cardiac mapping; utility or futility? Non-contact endocardial mapping" Indian Pacing and Electrophysiology Journal2:2Q-32 (2002).
He et al. "An equivalent body surface charge model representing three-dimensional bioelectrical activity" IEEE Transactions on Biomedical Engineering, 42.7 (1995) pp. 637-646.
International Search Report and Written Opinion in related Application No. PCT/US2012/028593 dated Mar. 5, 2013.
International Search Report in related Application No. PCT/IB2009/000071 dated Oct. 7, 2009.
Jackson, JD, "Surface Distributions of Charges and Dipoles and Discontinuities in the Electric Field and Potential", Classical Electrodynamics, 3rd edition, Dec. 1998, pp. 31-34.
Leif et al., "Geometric modeling based on polygonal meshes". Eurographics 2000 Tutorial, Aug. 21, 2000.
Office Action dated Mar. 9, 2016 in corresponding European Patent Application No. 09702094.5.
Partial European Search Report dated Apr. 29, 2014 in corresponding European Application No. 13176658.
Patent Examination Report No. 3 dated Sep. 21, 2016 in related Australian Application No. 2012225250.
Pullan et al. "The inverse problem of electrocardiology" Northeastern University Electrical and Computer Engineering, Feb. 23, 2007.
Van Oosterom A: "Solidifying the solid angle." 2002 Journal of Electrocardiology 2002 vol. 35 Suppl pp. 181-192 ISSN: 0022-0736.
William G. Stevenson et al: "Recording Techniques for Clinical Electrophysiology" Journal of Cardiovascular Electrophysiology. vol. 16 No. 91, Sep. 2005, pp. 1017-1022.
Wolfgang Nolting: Elektrodynamik—Grundkurs Theoretische Physik 3 Springer Spektrum pp. D 89-D 91.
Examination Report dated Jun. 27, 2017 issued in Australian Application No.
Australian Office Action dated Mar. 17, 2018 issued in Australian Application No. 2013308531.
Australian Office Action dated Feb. 26, 2018 issued in Australian Application No. 2017201560.
Office Action dated Jan. 31, 2018 issued for European Patent Application No. 13763151.1.
ISRWO dated Aug. 11, 2016 issued in corresponding International Application No. PCT/US2016/032017.
ISRWO dated Aug. 8, 2016 issued in corresponding European Application No. PCT/US2016/031823.
ISRWO dated Aug. 18, 2016 issued in corresponding International Application No. PCT/US16/32420.
ISRWO dated Dec. 12, 2017 issued in corresponding International Application No. PCT/US2017/056064.
ISRWO dated Sep. 25, 2017, issued in Application No. PCT/US17/30922.
ISRWO dated Aug. 4, 2017, issued in Application No. PCT/US17/30915.
European Office Action dated Apr. 23, 2018 issued in corresponding European Application No. 07785075.8.
Japanese Office Action dated Aug. 28, 2018 issued in corresponding Japanese Application No. 2016-542062, with machine translation into English.
Japanese Notice of Allowance dated Sep. 18, 2018 issued in corresponding Japanese Application No. 2015-557091, with English language translation.
Australian Examination Report dated Jun. 28, 2018, issued in corresponding Australian Patent Application No. 2014318872.
Patent Examination Report No. 2 dated Jun. 14, 2018 in related Australian Application No. 2014214756.
Canadian Office Action dated Nov. 7, 2018 issued in corresponding Canadian Application No. 2932956.
Extended European Search Report dated Dec. 5, 2018 issued in corresponding European Application No. 16793622.8.
Japanese Office Action dated Dec. 11, 2018 issued in corresponding Japanese Application No. 2018-024907, with machine translation to English.
Extended European Search Report dated Oct. 4, 2018 issued in corresponding European Application No. 16793503.0.
European Office Action dated Jan. 28, 2019 issued in corresponding European Application No. 14748567.6.
Australian Office Action dated Jan. 26, 2019 issued in corresponding Australian Application No. 2018211348.
Canadian Office Action dated Oct. 29, 2018 issued in corresponding Canadian Application No. 2829626.
Australian Examination Report dated Feb. 8, 2019 issued in corresponding Australian Application No. 2018250516.
Japanese Office Action dated Feb. 19, 2019 issued in corresponding Japanese Application No. 2016-558799, with machine translation to English.
Japanese Notice of Allowance dated Mar. 5, 2019 issued in corresponding Japanese Application No. 2018061040, with English translation.
European Office Action dated Feb. 6, 2019 issued in corresponding European Application No. 14843283.4.
Japanese Notice of Allowance dated Jun. 11, 2019 issued in corresponding Japanese Application No. 2018-024907, with English translation.
International Search Report and Written Opinion dated Apr. 8, 2019, issued in corresponding International Application No. PCT/US19/14498.
Japanese Office Action dated Jul. 23, 2019 issued in corresponding Japanese Application No. 2016-542062, with machine translation to English.
International Search Report and Written Opinion dated Jul. 23, 2019 issued in corresponding International Application No. PCT/US2019/031131.
Anatomy Warehouse, "Axis Heart Model", 2014, pp. 1-3, at http://www.anatomywarehouse.com/axis-scientitc-2-part-deluxe-life-size-human-heart-a-104269. (Year 2014).
Extended European Search Report dated Nov. 26, 2019 issued in corresponding European Application No. 19184148.5.
Japanese Office Action dated Oct. 15, 2019 issued in corresponding Japanese Application No. 2018-195960, with machine translation to English.
Canadian Office Action dated May 20, 2020 issued in corresponding Canadian Application No. 2881457.
European Office Action dated Jun. 15, 2020 issued in corresponding European Application No. 15768711.2.
Summons to Attend Oral Proceedings dated Dec. 20, 2019 issued in corresponding European Application No. 13763151.1.

(56) References Cited

OTHER PUBLICATIONS

Japanese Office Action dated Jan. 7, 2020 issued in corresponding Japanese Application No. 2016-558799, with machine translation to English.
Australian Office Action dated Jan. 15, 2020 issued in corresponding Australian Application No. 2016262547.
International Search Report and Written Opinion dated Jan. 14, 2020 issued in International Application No. PCT/US2019/060433.
Japanese Office Action dated Mar. 10, 2020 issued in corresponding Japanese Application No. 2017-559320, with machine translation to English.
Australian Office Action dated Mar. 26, 2020 issued in corresponding Australian Application No. 2016260522.
Australian Office Action dated Dec. 22, 2019 issued in corresponding Australian Application No. 2018278959.
Chinese Office Action dated Mar. 2, 2020 issued in corresponding Chinese Application No. 201680040709.1.
Australian Office Action dated Mar. 16, 2020 issued in corresponding Australian Application No. 2016260522.
Japanese Office Action dated Mar. 17, 2020 issued in corresponding Japanese Application No. 2019-071004, with machine translation to English.
Chinese Office Action dated Apr. 8, 2020 issued in corresponding Chinese Application No. 201810153436.2.
Japanese Notice of Allowance dated Jul. 7, 2020 issued in corresponding Japanese Application No. 2016558799, with English translation of allowed claims.
Japanese Office Action dated Jun. 30, 2020 issued in corresponding Japanese Application No. 2017559317, with machine translation to English.
International Search Report and Written Opinion dated Jul. 21, 2020 issued in corresponding International Application No. PCT/US2020/028779.
Japanese Office Action dated Jul. 28, 2020 issued in corresponding Japanese Application No. 2018-195960, with machine translation to English.
Japanese Notice of Allowance dated Sep. 1, 2020 issued in corresponding Japanese Application No. 2017-559320, with English summary.

* cited by examiner

DEVICES AND METHODS FOR DETERMINATION OF ELECTRICAL DIPOLE DENSITIES ON A CARDIAC SURFACE

RELATED APPLICATIONS

The present application claims priority under 35 USC 119(e) to U.S. Provisional Patent Application Ser. No. 61/877,617, entitled "Devices and Methods for Determination of Electrical Dipole Densities on a Cardiac Surface," filed Sep. 13, 2013, which is incorporated herein by reference in its entirety.

The present application, while not claiming priority to, may be related to U.S. patent application Ser. No. 13/858,715, entitled "Method and Device for Determining and Presenting Surface Charge and Dipole Densities on Cardiac Walls", filed Apr. 8, 2013, which is a continuation of U.S. Pat. No. 8,417,313 (hereinafter the '313 patent), entitled "Method and Device for Determining and Presenting Surface Charge and Dipole Densities on Cardiac Walls", issued Apr. 9, 2013, which was a 35 USC 371 national stage filing of PCT Application No. CH2007/000380, entitled "Method and Device for Determining and Presenting Surface Charge and Dipole Densities on Cardiac Walls", filed Aug. 3, 2007, published as WO 2008/014629, which claimed priority to Swiss Patent Application No. 1251/06 filed Aug. 3, 2006, each of which is hereby incorporated by reference.

The present application, while not claiming priority to, may be related to U.S. patent application Ser. No. 13/946,712, entitled "Device and Method for the Geometric Determination of Electrical Dipole Densities on the Cardiac Wall", filed Jul. 19, 2013, which is a continuation of U.S. Pat. No. 8,512,255, entitled "Device and Method for the Geometric Determination of Electrical Dipole Densities on the Cardiac Wall", issued Aug. 20, 2013, published as US2010/0298690 (hereinafter the '690 publication), which was a 35 USC 371 national stage application of Patent Cooperation Treaty Application No. PCT/IB09/00071 filed Jan. 16, 2009, entitled "A Device and Method for the Geometric Determination of Electrical Dipole Densities on the Cardiac Wall", published as WO2009/090547, which claimed priority to Swiss Patent Application 00068/08 filed Jan. 17, 2008, each of which is hereby incorporated by reference.

The present application, while not claiming priority to, may be related to U.S. application Ser. No. 14/003,671, entitled "Device and Method for the Geometric Determination of Electrical Dipole Densities on the Cardiac Wall", filed Sep. 6, 2013, which is a 35 USC 371 national stage filing of Patent Cooperation Treaty Application No. PCT/US2012/028593, entitled "Device and Method for the Geometric Determination of Electrical Dipole Densities on the Cardiac Wall", published as WO2012/122517 (hereinafter the '517 publication), which claimed priority to U.S. Patent Provisional Application Ser. No. 61/451,357, each of which is hereby incorporated by reference.

The present application, while not claiming priority to, may be related to Patent Cooperation Treaty Application No. PCT/US2013/057579, entitled "Catheter System and Methods of Medical Uses of Same, Including Diagnostic and Treatment Uses for the Heart", filed Aug. 30, 2013, which claims priority to U.S. Patent Provisional Application Ser. No. 61/695,535, entitled "System and Method for Diagnosing and Treating Heart Tissue", filed Aug. 31, 2012, which is hereby incorporated by reference.

The present application, while not claiming priority to, may be related to U.S. Patent Provisional Application Ser. No. 61/762,363, entitled "Expandable Catheter Assembly with Flexible Printed Circuit Board (PCB) Electrical Pathways", filed Feb. 8, 2013, which is hereby incorporated by reference.

FIELD

The present invention is generally related to treatment of cardiac arrhythmias, and more particularly to devices and methods for dipole density mapping.

BACKGROUND

For localizing the origin(s) of cardiac arrhythmias it is common practice to measure the electric potentials located on the inner surface of the heart by electrophysiological means within the patient's heart. One method is to insert electrode catheters into the heart to record cardiac potentials during normal heart rhythm or cardiac arrhythmia. If the arrhythmia has a regular activation sequence, the timing of the electric activation measured in voltages at the site of the electrode can be accumulated when moving the electrode around during the arrhythmia, to create a three-dimensional map of the electric activation. By doing this, information on the localization of the source of arrhythmia(s) and mechanisms, i.e., re-entry circuits, can be diagnosed to initiate or guide treatment (radiofrequency ablation). The information can also be used to guide the treatment of cardiac resynchronization, in which implantable pacing electrodes are placed in specific locations within the heart wall or chambers to re-establish a normal level of coordinated activation of the heart.

A method using external sensors measures the electrical activity of the heart from the body surface using electrocardiographic techniques that include, for example, electrocardiograms (ECG) and vectorcardiography (VCG). These external sensor techniques can be limited in their ability to provide information and/or data on regional electrocardiac activity. These methods can also fail to localize bioelectric events in the heart.

A method using external sensors for the localization of cardiac arrhythmias utilizes body surface mapping. In this technique, multiple electrodes are attached to the entire surface of the thorax and the information of the cardiac electrograms (surface ECG) is measured in voltages that are accumulated into maps of cardiac activation. This measurement can be problematic because the electrical activity is time dependent and spatially distributed throughout the myocardium and also fails to localize bioelectric events in the heart. Complex mathematical methods are required to determine the electric activation upon the outer surface of a heart model (i.e. epicardium), for instance, one obtained from CT or MRI imaging giving information on cardiac size and orientation within the thoracic cavity.

Alternatively, recordings of potentials at locations on the torso, for example, can provide body surface potential maps (BSPMs) over the torso surface. Although the BSPMs can indicate regional cardiac electrical activity in a manner that can be different from conventional ECG techniques, these BSPM techniques generally provide a comparatively low resolution, smoothed projection of cardiac electrical activity that does not facilitate visual detection or identification of cardiac event locations (e.g., sites of initiation of cardiac arrhythmias) and details of regional activity (e.g., number and location of arrythmogenic foci in the heart).

Since the localization of cardiac arrhythmias by the use of potentials is imprecise, the successful treatment of cardiac arrhythmias has been difficult and has demonstrated limited success and reliability. There is, therefore, a need for improved methods of localizing cardiac arrhythmias.

SUMMARY

In accordance with aspects of the present invention, provided are devices and methods for dipole density mapping, as well as methods for diagnosing tissue health. The present invention includes one or more electrodes configured to record electrical activity of tissue. In some embodiments, one or more ultrasound transducers, ultrasound sensors, and/or combinations of these can be included. The electrodes, transducers and sensors are located proximate the torso surface, and can be coupled to a wearable garment, such as a vest, shirt or bib. The device is constructed and arranged to produce continuous, real-time geometries of a patient's tissue, as well as information related to electrical activity present in the tissue.

The device can also be capable of providing tissue information, for example, tissue movement and tissue thickness. Additionally, the device can be configured to produce distance measurements by analyzing at least one of the sensors recorded angles or amplitudes or frequency changes. Non-limiting examples of distance measurements include: distance between the one or more electrodes and the epicardial surface and distance between the one or more electrodes and the one or more transducers and/or sensors.

The device can be configured to provide a tissue diagnostic through an analysis of both tissue motion information and cell electrical signals. The cell electrical signals can be recorded by the one or more electrodes, while tissue motion information can be gathered by the one or more electrodes and/or sensors. The device can be configured to provide exact foci and conduction-gap position information, such that ablation can be performed with an increased level of precision. Small conduction paths, including "gaps" in a line, are equally relevant as foci. The device can be used with an ablation device, such as robotic or manually controlled catheter ablation device. The device can also be used with a pacing system, such as a system for delivering pacing electrodes into the heart and for stimulating the heart with pacing pulses delivered through the pacing electrodes.

In accordance with one aspect of the present disclosure, a device generates a table of dipole densities $v(P',t)$ that embody an ionic nature of cellular membranes across the epicardium of a given heart of a patient. The device comprises: a measuring and recording unit that measures and records electric potential data Ve at given positions P proximate the patient's torso surface; an a/d-converter that converts the electric potential data Ve into digital voltage data; a processor that transforms the digital voltage data into cellular membrane dipole density data; and a memory that stores the electric potential data Ve and the transformed cellular membrane dipole density data.

In some embodiments, the measuring and recording unit includes multiple electrodes positioned proximate the patient's torso surface. The device can further comprise a wearable garment, and the multiple electrodes can be coupled to the wearable garment. The wearable garment can be flexible and conform closely to the patient's torso surface. The wearable garment can be configured to urge the multiple electrodes against the torso surface with a consistent position to prevent movement of at least one of the multiple electrodes.

In various embodiments, the wearable garment can be selected from the group consisting of: vest; shirt; bib; arm band; torso band; any patient-attachable assembly capable of maintaining the one or more electrodes in contact with the torso surface or sufficiently close thereto that a monitorable signal is detectable; and/or combinations thereof.

In some embodiments, the processor executes a computer program embodying an algorithm for transforming the digital voltage data into cellular membrane dipole density data. The computer program can be stored in a storage device, e.g., an electrical, magnetic, and/or optical storage device. The storage device can be a non-transitory storage device.

In some embodiments, the device further comprises one or more ultrasound transducers positioned proximate the patient's torso surface, the one or more ultrasound transducers being configured to emit waves toward an epicardial surface; and one or more ultrasound sensors positioned proximate the patient's torso surface, the one or more ultrasound sensors being configured to receive reflections of the waves from the epicardial surface and produce sensor data. The processor can be configured to receive the sensor data from the one or more sensors and generate distance measurements from the epicardial surface. The processor can be configured to produce the distance measurements by analyzing at least one of: timing of received signal; recorded signal amplitude; sensor recorded angle; or signal frequency changes.

The device can further comprise at least one wearable garment, and the at least one of the multiple electrodes, one or more ultrasound transducers, or one or more ultrasound sensors can be coupled to the at least one wearable garment. The at least one wearable garment can comprise a first wearable garment and a second wearable garment, and the multiple electrodes can be coupled to the first wearable garment, and the one or more ultrasound transducers and one or more ultrasound sensors can be coupled to the second wearable garment. In various embodiments, the at least one wearable garment can be selected from the group consisting of: vest; shirt; bib; arm band; torso band; any patient-attachable assembly capable of maintaining the one or more electrodes, one or more ultrasound transducers, and/or one or more ultrasound sensors in contact with the torso surface, or sufficiently close thereto that a monitorable signal is detectable; and/or combinations thereof.

In some embodiments, the device can be configured to diagnose at least one of: an arrhythmia; ischemia; or compromised myocardial function.

In some embodiments, the device can be configured to treat at least one of: an arrhythmia; ischemia; or compromised myocardial function.

In accordance with another aspect of the present disclosure, a device for creating a database of dipole densities d(y) at an epicardial surface of the heart of a patient comprises: multiple electrodes positioned proximate the patient's torso surface; a first receiver configured to receive mapping information from the multiple electrodes; a second receiver configured to receive an anatomical depiction of the heart; a dipole density module configured to generate the database of dipole densities d(y) of polygonal shaped projections onto the epicardial surface, wherein the dipole density module computes the dipole density at all vertices of the polygonal shaped projections, wherein if the dipole density is d(y), the total measured potential V(x) at a location x is the sum over all vertices of d(y) times a matrix $\omega(x,y)$, and wherein: a) x represents a series of locations on the torso surface; and b) V(x) is a measured potential at point x, said measured potential recorded by the multiple electrodes.

In some embodiments, the dipole density module can generates the database of dipole densities d(y) using a finite elements method.

In some embodiments, the polygonal shaped projections can be substantially the same size.

In some embodiments, the dipole density can be determined by a number of polygonal shaped projections, wherein the number can be determined by the size of the epicardial surface.

In some embodiments, the polygonal shaped projections can be selected from the group consisting of: triangles; squares; tetrahedral shapes; hexagonal shapes; any other suitable shape compatible with finite elements method; and/or combinations thereof.

In some embodiments, the device can further comprise a wearable garment, and the multiple electrodes can be coupled to the wearable garment. The wearable garment can be flexible and conform closely to the patient's torso surface. The wearable garment can be configured to urge the multiple electrodes against the torso surface with a consistent position to prevent movement of the electrodes. The wearable garment can be selected from the group consisting of: vest; shirt; bib; arm band; torso band; any patient-attachable assembly capable of maintaining the one or more electrodes in contact with the torso surface or sufficiently close thereto that a monitorable signal is detectable; and/or combinations thereof.

In some embodiments, the anatomical depiction of the heart can comprise previous anatomical imaging and/or real-time anatomical imaging from one or more of CT; MRI; internal ultrasound; external ultrasound; or other imaging apparatus.

In some embodiments, the anatomical depiction of the heart can comprise a generic model of a heart.

In some embodiments, the device can further comprise: one or more ultrasound transducers positioned proximate the patient's torso surface, the one or more ultrasound transducers being configured to emit waves toward the epicardial surface; and one or more ultrasound sensors positioned proximate the patient's torso surface, the one or more ultrasound sensors being configured to receive reflections of the waves from the epicardial surface.

The device can further comprise at least one wearable garment, and at least one of the multiple electrodes, one or more ultrasound transducers, and/or one or more ultrasound sensors can be coupled to the at least one wearable garment. The at least one wearable garment can comprise a first wearable garment and a second wearable garment, and the multiple electrodes can be coupled to the first wearable garment, and the one or more ultrasound transducers and/or one or more ultrasound sensors can be coupled to the second wearable garment. The at least one wearable garment can be selected from the group consisting of: vest; shirt; bib; arm band; torso band; any patient-attachable assembly capable of maintaining the one or more electrodes, one or more ultrasound transducers, and/or one or more ultrasound sensors in contact with the torso surface, or sufficiently close thereto that a monitorable signal is detectable; and/or combinations thereof. The anatomical depiction of the heart can comprise real-time anatomical imaging from the one or more ultrasound transducers and the one or more ultrasound sensors.

In some embodiments, the device can be configured to diagnose at least one of: anarrhythmia; ischemia; or compromised myocardial function.

In some embodiments, the device can be configured to treat at least one of: an arrhythmia; ischemia; or compromised myocardial function.

In accordance with another aspect of the present disclosure, a method of creating a database of dipole densities d(y) at the epicardial surface of the heart of a patient comprises: placing an array of multiple electrodes proximate the patient's torso surface; and calculating dipole densities d(y) by: receiving mapping information from the multiple electrodes; receiving an anatomical depiction of the heart; and generating the database of dipole densities d(y) with a dipole density module, wherein the dipole density module determines dipole densities d(y) of polygonal shaped projections onto the epicardial surface, wherein the dipole density module computes the dipole density at all vertices of the polygonal shaped projections, wherein if the dipole density is d(y), the total measured potential V(x) at a location x is the sum over all vertices of d(y) times a matrix $\omega(x,y)$, and wherein: a) x represents a series of locations on the torso surface; and b) V(x) is a measured potential at point x, said measured potential recorded by the multiple electrodes.

In some embodiments, the dipole density module can generate the database of dipole densities d(y) using a finite elements method.

In some embodiments, the method can further comprise providing a wearable garment, and the multiple electrodes can be coupled to the wearable garment. The wearable garment can be configured to urge the multiple electrodes against the torso surface with a consistent position to prevent movement of the electrodes. The wearable garment can be selected from the group consisting of: vest; shirt; bib; arm band; torso band; any patient-attachable assembly capable of maintaining the one or more electrodes in contact with the torso surface or sufficiently close thereto that a monitorable signal is detectable; and/or combinations thereof.

In some embodiments, the method can include using the dipole densities d(y) to locate an origin of abnormal electrical activity of a heart.

In some embodiments, the method can include using the dipole densities d(y) to diagnose at least one of: an arrhythmia; ischemia; or compromised myocardial function.

In some embodiments, the method can include using the dipole densities d(y) to treat at least one of: an arrhythmia; ischemia; or compromised myocardial function.

In some embodiments, calculating the dipole densities d(y) can include a processor executing a computer program stored in a memory, the computer program embodying an algorithm for generating a table of dipole densities in the memory. The memory can be a non-transitory storage device, such as an electrical, magnetic, and/or optical storage device, as examples.

In accordance with another aspect of the present disclosure, a device for creating a database of dipole densities d(y) and distance measurements at an epicardial surface of a patient comprises: an array of multiple electrodes positioned proximate the patient's torso surface; one or more ultrasound transducers positioned proximate the patient's torso surface, the one or more ultrasound transducers being configured to emit waves toward the epicardial surface; one or more ultrasound sensors positioned proximate the patient's torso surface, the one or more ultrasound sensors being configured to receive reflections of the waves from the epicardial surface; and a computer coupled to the multiple electrodes, one or more ultrasound transducers, and one or more ultrasound sensors, wherein the computer is configured to receive mapping information from the multiple electrodes and sensor data from the one or more sensors, and generate the database of dipole densities d(y) and distance measurements.

In some embodiments, the device can further comprise at least one wearable garment, and at least one of the multiple electrodes, one or more ultrasound transducers, and/or one or more ultrasound sensors can be coupled to the at least one wearable garment. The wearable garment can be flexible and conform closely to the body of the patient. The wearable garment can be configured to urge electrodes, sensors and/or transducers against the torso surface with a consistent position to prevent movement of the electrodes, sensors and/or transducers. The at least one wearable garment can be selected from the group consisting of: vest; shirt; bib; arm band; torso band; any patient-attachable assembly capable of maintaining the one or more electrodes, one or more ultrasound transducers, and one or more ultrasound sensors in contact with the torso surface, or sufficiently close thereto that a monitorable signal is detectable; and combinations thereof.

In various embodiments, the at least one wearable garment can comprise a first wearable garment and a second wearable garment, and the multiple electrodes can be coupled to the first wearable garment, and the one or more ultrasound transducers and/or one or more ultrasound sensors can be coupled to the second wearable garment. The computer can be coupled to the wearable garment.

In some embodiments, the computer can include: a dipole density module configured to generate a three dimensional database of dipole densities $d(y)$, and wherein the dipole density module determines a dipole density for polygonal shaped projections onto the epicardial surface and computes the dipole density at all vertices of the polygonal shaped projections, wherein if the dipole density is $d(y)$, the total measured potential $V(x)$ at a location x is the sum over all vertices of $d(y)$ times a matrix $\omega(x,y)$, and wherein: a) x represents a series of locations on the torso surface; and b) $V(x)$ is a measured potential at point x, said measured potential recorded by the multiple electrodes. The dipole density module can generate the database of dipole densities $d(y)$ using a finite elements method. The polygonal shaped projections can be substantially the same size. The dipole density can be determined by a number of polygonal shaped projections, the number determined by the size of an epicardial surface. Such module can include or be embodied in, as examples, hardware, computer program code, firmware, and/or combinations thereof.

In some embodiments, the device can be configured to provide epicardial surface motion information of the heart. The device can be configured to provide tissue diagnostic information by analyzing both motion information and cell electrical signals. The cell electrical signals can be recorded by the multiple electrodes.

In some embodiments, the device can further include a display configured to display real time motion.

In some embodiments, the computer can be configured to produce a geometrical depiction of the heart.

In some embodiments, the device can be further configured to determine properties of the cardiac wall. The properties can include cardiac wall thickness information. The properties can include precise foci, conduction-gaps, and/or conduction channels position information.

In some embodiments, the distance measurement can comprise the distance between at least one of the multiple electrodes and at least one epicardial surface.

In some embodiments, the device can be configured to produce the distance measurement by analyzing at least one of: timing of received signal; recorded signal amplitude; sensor recorded angle; or signal frequency changes.

In some embodiments, the device can be configured to provide epicardial surface information during a cardiac ablation procedure. The ablation procedure can comprise delivery of RF, ultrasound, microwave, cryogenic and/or laser energy to tissue.

In some embodiments, at least one of the sensors and at least one of the transducers can comprise a single component.

In some embodiments, at least one of the sensors and at least one of the transducers can be integral to at least one electrode of the multiple electrodes.

In some embodiments, the computer can be configured to determine a map of dipole densities $d(y)$ at corresponding time intervals.

In some embodiments, the computer can be configured to generate a synthesis of maps that represents a cascade of activation sequences of each corresponding heart beat from a series of heart beats.

In some embodiments, the device can be configured to diagnose at least one of: an arrhythmia; ischemia; or compromised myocardial function.

In some embodiments, the device can be configured to treat at least one of: an arrhythmia; ischemia; or compromised myocardial function.

In accordance with another aspect of the present disclosure, a method of creating a database of dipole densities $d(y)$ and distance measurements at an epicardial surface of a patient comprises: placing an array of multiple electrodes, one or more ultrasound transducers, and one or more ultrasound sensors proximate the patient's torso surface; and calculating dipole densities $d(y)$ by: receiving mapping information from the multiple electrodes; emitting waves toward the epicardial surface with the one or more ultrasound transducers; receiving reflections of the waves from the epicardial surface with the one or more ultrasound sensors; producing a geometrical depiction of the epicardial surface; generating the database of dipole densities $d(y)$ with a dipole density module, wherein the dipole density module determines dipole densities $d(y)$ of polygonal shaped projections onto the epicardial surface, wherein the dipole density module computes the dipole density at all vertices of the polygonal shaped projections, wherein if the dipole density is $d(y)$, the total measured potential $V(x)$ at a location x is the sum over all vertices of $d(y)$ times a matrix $\omega(x,y)$, and wherein: a) x represents a series of locations on the torso surface; and b) $V(x)$ is a measured potential at point x, said measured potential recorded by the multiple electrodes; and calculating distance or movement information by analyzing signals received from the sensor.

In some embodiments, the dipole density module can be configured to generate the database of dipole densities $d(y)$ using a finite elements method.

In some embodiments, the method can further comprise providing at least one wearable garment, wherein at least one of the multiple electrodes, one or more ultrasound transducers, and one or more ultrasound sensors can be coupled to the at least one wearable garment. The at least one wearable garment can be configured to urge the electrodes, sensors and/or transducers against the torso surface with a consistent position to prevent movement of the electrodes, sensors and/or transducers. The at least one wearable garment can be selected from the group consisting of: vest; shirt; bib; arm band; torso band; any patient-attachable assembly capable of maintaining the one or more electrodes in contact with the torso surface or sufficiently close thereto that a monitorable signal is detectable; and/or combinations thereof.

In various embodiments, the at least one wearable garment can comprise a first wearable garment and a second wearable garment and the multiple electrodes can be coupled to the first wearable garment, and the one or more ultrasound transducers and one or more ultrasound sensors can be coupled to the second wearable garment.

In some embodiments, calculating distance information can comprise calculating tissue thickness information.

In some embodiments, the method can include using the dipole densities d(y) to locate an origin of abnormal electrical activity of a heart.

In some embodiments, the method can include using the dipole densities d(y) to diagnose at least one of: an arrhythmia; ischemia; or compromised myocardial function.

In some embodiments, the method can include using the dipole densities d(y) to treat at least one of: an arrhythmia; ischemia; or compromised myocardial function.

In some embodiments, calculating the dipole densities d(y) can include a processor executing a computer program stored in a memory, the computer program embodying an algorithm for generating a table of dipole densities in the memory.

In some embodiments, at least one ultrasound transducer can comprise at least one ultrasound sensor.

In accordance with another aspect of the present disclosure, a device for creating a database of dipole densities d(y) at the epicardial surface and endocardial surface of the heart of a patient comprises: an external array of multiple electrodes positioned proximate the patient's torso surface; an internal array of multiple electrodes positioned within a chamber of the heart; a first receiver configured to receive mapping information from the external and internal array of multiple electrodes; a second receiver configured to receive an anatomical depiction of the heart; a dipole density module configured to generate the database of dipole densities d(y) of polygonal shaped projections onto the epicardial surface and endocardial surface, wherein the dipole density module computes the dipole density at all vertices of the polygonal shaped projections, wherein if the dipole density is d(y), the total measured potential V(x) at a location x is the sum over all vertices of d(y) times a matrix ω(x,y), and wherein: a) x represents a series of locations on the torso surface; and b) V(x) is a measured potential at point x, said measured potential recorded by the multiple electrodes.

In some embodiments, the dipole density module can be configured to generate the database of dipole densities d(y) using a finite elements method.

In some embodiments, the polygonal shaped projections can be substantially the same size.

In some embodiments, the dipole density can be determined by a number of polygonal shaped projections, wherein the number can be determined by the size of an epicardial surface and endocardial surface.

In some embodiments, the device can further comprise a wearable garment, and the external array of multiple electrodes can be coupled to the wearable garment.

In some embodiments, the device can further comprise a catheter, and the internal array of multiple electrodes can be coupled to the catheter.

In some embodiments, the anatomical depiction of the heart can comprise a generic model of a heart.

In some embodiments, the device can further comprise: one or more external ultrasound transducers positioned proximate the patient's torso surface, the one or more ultrasound transducers being configured to emit waves toward the epicardial surface; and one or more external ultrasound sensors positioned proximate the patient's torso surface, the one or more ultrasound sensors being configured to receive reflections of the waves from the epicardial surface.

The device can further comprise at least one wearable garment, and the at least one of the multiple external electrodes, one or more external ultrasound transducers, or one or more external ultrasound sensors can be coupled to at least one wearable garment. The anatomical depiction of the epicardial surface of the heart can comprise real-time anatomical imaging from the one or more external ultrasound transducers and the one or more external ultrasound sensors.

In some embodiments, the device can further comprise: one or more internal ultrasound transducers positioned within a chamber of the heart, the one or more ultrasound transducers being configured to emit waves toward the endocardial surface; and one or more internal ultrasound sensors positioned within a chamber of the heart, the one or more ultrasound sensors being configured to receive reflections of the waves from the endocardial surface. The at least one of the multiple internal electrodes, one or more internal ultrasound transducers, or one or more internal ultrasound sensors can be coupled to a catheter. The anatomical depiction of the endocardial surface of the heart can comprise real-time anatomical imaging from the one or more internal ultrasound transducers and the one or more internal ultrasound sensors.

In some embodiments, the device can be configured to diagnose at least one of: an arrhythmia; ischemia; or compromised myocardial function.

In some embodiments, the device can be configured to treat at least one of: an arrhythmia; ischemia; or compromised myocardial function.

In accordance with another aspect of the present disclosure, a portable system for obtaining mapping information at an epicardial surface of the heart of a patient comprises: a wearable garment proximate the patient's torso; an array of multiple electrodes coupled to the wearable garment proximate the patient's torso surface; and a device configured to receive mapping information from the multiple electrodes.

In some embodiments, the multiple electrodes can be wired and/or wirelessly connected to the device.

In some embodiments, the device can include a recording device configured to record the mapping information.

In some embodiments, the device can include a communication system configured to transmit the mapping information to a remote location.

In some embodiments, the device can include a computer configured to receive the mapping information from the multiple electrodes and generate a database of dipole densities d(y). The computer can be further configured to transmit the mapping information and/or dipole densities d(y) to a remote location.

In some embodiments, the device can be coupled to the wearable garment.

In some embodiments, the portable system can further comprise: one or more ultrasound transducers coupled to the wearable garment, the one or more ultrasound transducers being configured to emit waves toward the epicardial surface; and one or more ultrasound sensors coupled to the wearable garment, the one or more ultrasound sensors being configured to receive reflections of the waves from the epicardial surface; wherein the portable system is configured to receive information from the ultrasound sensors. The portable system can include a recording device coupled to the one or more ultrasound sensors and configured to receive and record sensor data from the one or more ultrasound sensors. The portable system can include a communication system coupled to the one or more ultrasound transducers and one or more ultrasound sensors and configured to transmit the sensor data from the one or more sensors to a remote location. The portable system can include a computer coupled to the one or more ultrasound transducers and one or more ultrasound sensors, and the computer can be configured to receive sensor data from the one or more sensors and to determine distance measurements to the epicardial surface.

In some embodiments, the portable system can further comprise one or more functional elements, the one or more functional elements comprising one or more elements selected from the group consisting of: a pressure sensor such as a blood pressure sensor; a pH sensor; a glucose sensor; a respiration sensor; a salinity or other sweat level sensor; an EEG sensor such as an EEG sensor placed on the scalp of the patient; an oxygen level sensor such as an oxygen level sensor placed on the finger of the patient; an eye gaze sensor; and/or combinations of these. The one or more functional elements can be coupled to the wearable garment. The portable system can include a recording device operably coupled to the one or more functional elements and configured to receive and record data from the one or more functional elements. The portable system can include a communication system operably coupled to the one or more functional elements and configured to transmit data from the one or more functional elements to a remote location. The portable system can include a computer operably coupled to the one or more functional elements, and the computer can be configured to receive data from the one or more functional elements. The computer can comprise one or more algorithms constructed and arranged, when executed by at least one computer processor, to analyze one or more of: cardiac geometry; cardiac electrical activity; blood pressure; pH; glucose; respiration; sweat level; brain activity; and/or blood oxygen level. The computer can be configured to analyze cardiac electrical activity and at least one physiologic parameter selected from the group consisting of: blood pressure; pH; glucose; respiration; sweat level; brain activity; and/or blood oxygen level.

In some embodiments, the system can be configured to diagnose at least one of: an arrhythmia; ischemia; or compromised myocardial function.

In some embodiments, the system can be configured to treat at least one of: an arrhythmia; ischemia; or compromised myocardial function.

In accordance with another aspect of the present disclosure, a portable system for obtaining information at an epicardial surface of the heart of a patient comprises: a wearable garment positioned proximate the patient's torso surface having array of multiple electrodes, one or more transducers, one or more sensors and/or one or more functional elements coupled to the wearable garment; and a portable device configured to receive information from the electrodes, transducers, sensors and/or functional elements.

In some embodiments, the wearable garment can be selected from the group consisting of: vest; shirt; bib; arm band; torso band; any patient-attachable assembly capable of maintaining the one or more electrodes, one or more ultrasound transducers, and/or one or more ultrasound sensors in contact with the torso surface, or sufficiently close thereto that a monitorable signal is detectable; and/or combinations thereof.

In some embodiments, the functional elements can include an element selected from the group consisting of: a pressure sensor such as a blood pressure sensor; a pH sensor; a glucose sensor; a respiration sensor; a salinity or other sweat level sensor; an EEG sensor such as an EEG sensor placed on the scalp of the patient; an oxygen level sensor such as an oxygen level sensor placed on the finger of the patient; an eye gaze sensor; and/or combinations of these. The portable system can include a computer, and the computer can comprise one or more algorithms constructed and arranged to, when executed by at least one computer processor, analyze one or more of: cardiac geometry; cardiac electrical activity; blood pressure; pH; glucose; respiration; sweat level; brain activity; and blood oxygen level. The computer can be configured to analyze cardiac electrical activity and at least one physiologic parameter selected from the group consisting of: blood pressure; pH; glucose; respiration; sweat level; brain activity; and/or blood oxygen level.

In some embodiments, the wearable garment includes multiple wearable garments, and the array of multiple electrodes, one or more transducers, one or more sensors and/or one or more functional elements can be coupled to one or more of the multiple wearable garments.

In some embodiments, the portable system includes a computer coupled to the multiple electrodes and the computer can include one or more algorithms constructed and arranged to analyze mapping information from the multiple electrodes and generate the database of dipole densities d(y).

In some embodiments, the portable system includes a computer coupled to the one or more ultrasound transducers and one or more ultrasound sensors: the one or more ultrasound transducers being configured to emit waves toward the epicardial surface; the one or more ultrasound sensors being configured to receive reflections of the waves from the epicardial surface; and wherein the computer includes one or more algorithms constructed and arranged to receive sensor data from the one or more sensors to determine distance measurements to the epicardial surface.

In some embodiments, the system can be configured to diagnose at least one of: an arrhythmia; ischemia; or compromised myocardial function.

In some embodiments, the system can be configured to treat at least one of: an arrhythmia; ischemia; or compromised myocardial function.

DETAILED DESCRIPTION

Figure 1:
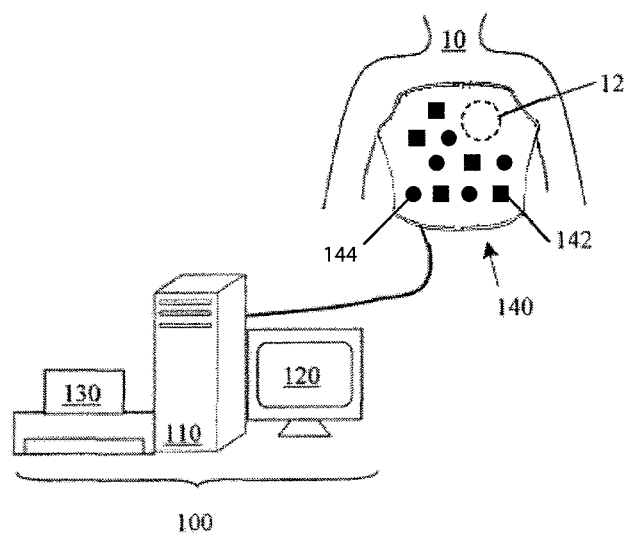
FIG. 1 illustrates an exemplary embodiment of a mapping system, in accordance with aspects of the present invention.

Various exemplary embodiments will be described more fully hereinafter with reference to the accompanying drawings, in which some exemplary embodiments are shown. The present inventive concept can, however, be embodied in many different forms and should not be construed as limited to the exemplary embodiments set forth herein.

It will be understood that, although the terms first, second, etc. are used herein to describe various elements, these elements should not be limited by these terms. These terms are used to distinguish one element from another, but not to imply a required sequence of elements. For example, a first element can be termed a second element, and, similarly, a second element can be termed a first element, without departing from the scope of the present invention. As used herein, the term "and/or" includes any and all combinations of one or more of the associated listed items.

It will be understood that when an element is referred to as being "on" or "attached", "connected" or "coupled" to another element, it can be directly on or connected or coupled to the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, steps, operations, elements, and/or components, but do not preclude the presence or addition of one or more other features, steps, operations, elements, components, and/or groups thereof.

Spatially relative terms, such as "beneath," "below," "lower," "above," "upper" and the like can be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in the figures is turned over, elements described as "below" and/or "beneath" other elements or features would then be oriented "above" the other elements or features. The device can be otherwise oriented (e.g., rotated 90 degrees or at other orientations) and the spatially relative descriptors used herein interpreted accordingly.

Various exemplary embodiments are described herein with reference illustrations of idealized or representative structures and intermediate structures. As such, variations from the shapes of the illustrations as a result, for example, of manufacturing techniques and/or tolerances, are to be expected. Thus, exemplary embodiments should not be construed as limited to the particular shapes of regions illustrated herein but are to include deviations in shapes that result, for example, from manufacturing.

The catheters and other devices described in accordance with aspects of the present invention can include numerous forms of diagnostic catheters, such as catheters including one or more electrodes, or therapeutic catheters such as tissue ablation catheters. Catheters can be introduced percutaneously into a patient's heart, such as to record electrical activity, measure distances between structures, or deliver energy. External devices and systems can be included, such as body surface electrodes used to record electrical activity or deliver an electric signal, or visualization devices such as external ultrasound or fluoroscopic imaging systems. Any of these catheters or other devices can include one or more electrodes and/or one or more ultrasound elements (e.g. one or more ultrasound sensors and/or ultrasound transducers). The electrodes and/or ultrasound elements of the present invention can be positioned at any location on the device, for example at a distal or proximal portion of the device, and can be positioned internal or external to a patient's body.

Any or all of the ultrasound elements (e.g. ultrasound transducers and/or ultrasound sensors) of the present invention can be used to measure a distance between a sensor and/or a transducer and a surface, as is known in the art. One example includes measuring the distance between an ultrasound element comprising a sensor-transducer pair and a wall of a chamber of the heart.

Any or all of the electrodes of the present invention can be used to record electric "signals" (e.g. voltages and/or currents) at or between one or more electrode locations. Recorded electric signals can be used to map electrical activity of tissue. The mapped electrical activity can be further processed (e.g. in terms of sources of charge and charge density and correlated with various physiologic parameters related to the function of the heart) and the mapped electrical activity and other recorded and calculated information can be provided visually to one or more operators of the system of the present invention.

Any or all of the electrodes of the present invention can be used to deliver and/or record electric signals that are generated by the system. Such delivered signals can be emitted from any one or more electrodes, and can be delivered between any two or more electrodes. Recorded signals can comprise a signal present at a single electrode location or at multiple electrode locations (e.g. a signal representing a comparison of two or more signals present at two or more electrode locations). Recorded signals can be measured, for example, synchronously or asynchronously in terms of voltage and/or current. Recorded signals can be further processed in terms of, for example, resistive and reactive components of impedance and/or the combined magnitude of impedance with any original or processed signal "values" (e.g. those represented by a parameter selected from the group consisting of: instantaneous amplitude; phase; peak; Root-Mean-Square (rms); demodulated magnitude; and combinations of these).

The terms "map" and "mapping" shall include, but need not be limited to, "electrical map", "electrical mapping", "anatomical map", "anatomical mapping", "device map" and "device mapping", each of which is defined herein below.

The terms "electrical map" and "electrical mapping" shall include, but need not be limited to, recording, processing and/or displaying electrical information, such as electrical information recorded by one or more electrodes described or understood in accordance with the present invention. This electrical information includes, but is not limited to: cardiac or other tissue voltage measurements; cardiac or other tissue bipolar and/or unipolar electrograms; cardiac or other tissue surface charge data; cardiac or other tissue dipole density data; cardiac or other tissue monophasic action potentials; and combinations of these.

The terms "anatomical map" and "anatomical mapping" shall include, but need not be limited to, recording, processing and/or displaying anatomical information, such as anatomical information provided by one or more ultrasound elements of the present invention and/or one or more electrodes described or understood in accordance with the present invention. This anatomical information includes, but is not limited to: two-dimensional (2D) or three-dimensional (3D) representations of tissue, such as one or more chambers of a heart; tissue wall thicknesses such as the thickness of an atrial or ventricular wall; distance between two tissue surfaces; and combinations of these. In some embodiments, a dipole density map and/or surface charge map (hereinafter singly or collectively dipole density map) is provided by using information provided by multiple electrodes and multiple ultrasound elements, such as is described in Applicant's co-pending international application, Serial Number PCT/US2012/028593, entitled "Device and Method For the Geometric Determination of Electrical Dipole Densities on the Cardiac Wall", the entirety of which is incorporated herein.

The terms "device map" and "device mapping" shall include, but need not be limited to, recording, processing and/or displaying of device distance information, such as information comprising the distance between a device or device component and another object, such as tissue or another device or device component.

Any pair of electrodes described or understood in accordance with the present invention can be constructed and arranged to provide distance information, such as the distance between that pair of electrodes, or the distance between one of the electrodes and one or more proximate components (e.g. a component at a known distance from one or both of the electrodes in the pair). By delivering and recording an electric signal between electrodes of known separation distances, the signal can by processed and/or calibrated according to one or more known separation distances (e.g. the separation distance between two electrodes fixedly mounted to a rigid structure at a pre-determined distance). Calibrated signal values can be combined across adjacent sets of electrode pairs to accurately estimate the distance between any pair (e.g. any arbitrary pair of electrodes on any one or more devices of the system) of electrodes for which the separation distance is not known. Known and calculated separation distances can be used as "reference" electrodes and combined to triangulate the unknown position of one or more "marker" electrodes, such as an electrode positioned on the present invention or on a separate or external device and positioned proximate the present invention. The process of triangulation can be used to dynamically localize the three-dimensional position of any or all of the electrodes either individually and/or as a combined entity in three-dimensional space.

Further, any or all electrodes described or understood in accordance with the present invention, such as one or more electrodes placed inside a chamber of a heart, can be used to deliver electric energy, such as radiofrequency energy.

In accordance with aspects of the present invention, provided is an improved device, system and method for calculating and visualizing the distribution and activity of dipole densities and/or surface charge (hereinafter singly or collectively dipole densities) on the epicardial surface of the heart, and in some embodiments, dipole densities on both the epicardial and endocardial surfaces simultaneously. The dipole densities can be determined by a finite elements method, avoiding the errors encountered using previous extrapolation algorithms.

Calculating surface charge and/or dipole densities of the heart with internal electrodes has been described in detail in U.S. Pat. No. 8,417,313 (hereinafter the '313 patent), entitled "Method and device for determining and presenting surface charge and dipole densities on cardiac walls".

As discussed in the '313 patent, research indicated that the use of the surface charge densities (i.e. their distribution) or dipole densities (i.e. their distribution) to generate distribution map(s) would lead to more detailed and precise information on electric ionic activity of local cardiac cells than potentials. Surface charge density or dipole densities represent precise information of the electric activity with a compact spatial resolution, whereas potentials resulting from integration of charge densities provide only a diffuse picture of electric activity. The electric nature of cardiac cell membranes comprising ionic charges of proteins and soluble ions can be precisely described by surface charge and dipole densities. The surface charge densities or dipole densities cannot be directly measured in the heart, but instead must be mathematically and accurately calculated starting from measured potentials. In other words, the information of voltage maps obtained by current mapping systems can be greatly refined when calculating surface charge densities or dipole densities from these.

The surface charge density means surface charge (Coulombs) per unit area ($cm^2$). A dipole, as such, is a neutral element, wherein a part comprises a positive charge and the other part comprises the same but negative charge. A dipole can better represent the electric nature of cellular membranes, because in a biological environment ion charges are not macroscopically separated.

A device for determining dipole densities on the heart wall with internal electrodes has been described in detail in U.S. Patent Publication No. US2010/0298690 (hereinafter the '690 publication) and Patent Cooperation Treaty Publication No. WO2012/122517 (hereinafter the '517 publication), entitled "Device and method for the geometric determination of electrical dipole densities on the cardiac wall.

The '517 publication disclosed devices, systems, and methods for determining the dipole densities on heart walls using one or more catheters placed into the heart chamber. In particular, a triangularization of the heart wall is performed in which the dipole density at each vertex correlate to the potential measured at various locations within the associated chamber of the heart. To create a database of dipole densities, mapping information recorded by one or more electrodes located on one or more catheters and anatomical information is used. Additionally, one or more ultrasound elements are provided on the catheter.

While the '313 patent, '690 publication and '517 publication disclose devices, systems, and methods for creating an image of the heart based on information recorded from one or more internal electrodes (e.g. creating an anatomical and/or electrical representation of the heart), some embodiments of the present invention disclose devices, systems, and methods for creating a heart image with external sensors (i.e. external sensors only), while other embodiments disclose devices, systems, and methods using both internal and external sensors to create the heart image.

For imaging of the heart with external sensors, one or more electrodes outside the body (external) can be positioned proximate the surface of the patient's torso. In some embodiments, one or more ultrasound elements (e.g. one or more ultrasound transducers, sensors or combined transducer-sensors, hereinafter "ultrasound element") can also be used with the one or more electrodes outside the body, such as one or more ultrasound elements also positioned proximate the surface of the patient's torso.

For the combination of signals from both external and internal sensors to create an image of the heart, the external one or more electrodes disclosed in the present invention are used with internal (inside the body) electrodes disclosed in the internal sensor-based devices, systems, and methods of the '313 patent, '690 publication and '517, combining heart chamber geometry with internal and external sensor (voltage) readings, such that dipole densities can be depicted as an animated color map of activation for each heart beat across the epicardial and/or endocardium surface. The information can be used to diagnose and/or treat a patient with a cardiac arrhythmia, such as atrial fibrillation, or an inadequately synchronized activation sequence, such as in heart failure. Other information obtained can include precise location of foci, conduction-gaps, and/or position of conduction channels.

In some embodiments of the present invention, a dipole density library can be created in computer memory by combining the electrode voltage readings from one or more electrodes proximate the surface of the patient's torso with anatomical imaging from an imaging instrument, such as CT; MRI; ultrasound; and/or a generic model of a heart. This anatomical imaging can be generated in real-time and/or imported from previous imaging from one or more of CT, MRI, ultrasound (internal or external), or other imaging apparatus.

In some embodiments of the present invention, the dipole density library is created by combining the electrode voltage readings from one or more electrodes with ultrasound readings recorded by the one or more ultrasound elements proximate the surface of the patient's torso. Alternatively or additionally, the dipole density library is created by combining the electrode voltage readings from one or more electrodes with ultrasound readings recorded by one or more ultrasound elements positioned within the patient's body, such as one or more ultrasound elements positioned within one or more chambers of the patient's heart.

In some embodiments, the system of the present invention comprises an external device, for example a vest, having one or more electrodes, and optionally, one or more ultrasound elements. FIG. 1 shows an example embodiment of a mapping system 100 that can be used for real time dipole density mapping of a heart 12 of a human 10. System 100 can include a computer 110 having known types of input devices and output devices, such as a display 120 and printer 130, coupled to a patient attachment device, vest 140, having one or more electrodes 142. In some embodiments, vest 140 can further include one or more ultrasound elements 144. Ultrasound elements 144 can include one or more ultrasound transducers configured to transmit ultrasound waves, such as sound waves configured to reflect off of one or more structures of the heart, and be recorded or otherwise received by one or more ultrasound sensors. Alternatively or additionally, ultrasound elements 144 can include one or more ultrasound sensors, such as one or more ultrasound sensors which receive the reflected sound waves. In some embodiments, one or more ultrasound elements 144 can include both an ultrasound transmitter and an ultrasound sensor, such as a single element that both transmits and receives ultrasound waves.

While a vest is shown, numerous alternative patient attachment device types can be used, including, for example, shirts, bibs, arm bands, torso bands and/or any other patient-attachable assembly capable of maintaining the one or more electrodes 142 and/or ultrasound elements 144 in contact with the wearer's body, or sufficiently close thereto, such that a signal can be detected and/or transmitted by each signal-detecting element. Alternatively or additionally, the one or more electrodes 142 and/or ultrasound elements 144 can be attached directly to the skin. In some embodiments, multiple discrete attachments can be used with a combination of garments, (e.g. shirt plus armband or torso band plus armband), or a combination of a garment with direct skin attachment(s).

In some embodiments, vest 140 can only include one or more electrodes 142, with no ultrasound elements. In other embodiments, vest 140 can include one or more ultrasound elements 144, and not have any electrodes. In still other embodiments a combination of garments can be used with different elements being positioned on different garments. For example, in a combination of shirt plus armband, the shirt can have one or more electrodes 142 while the armband can have one or more ultrasound elements 144.

In some embodiments, vest 140 is flexible and conforms closely to the body of the patient and can be made of any suitable materials. Vest 140 can be configured so that the one or more electrodes 142 and/or ultrasound elements 144 are urged against the skin at a consistent position, such as to prevent movement of the element across the skin. In some embodiments, the one or more electrodes 142 and/or ultrasound elements 144 can be positioned on both the front and the back of the patient. In other embodiments, the one or more electrodes 142 and/or ultrasound elements 144 can be positioned only on the front or back of the patient, depending on application.

Figure 8:
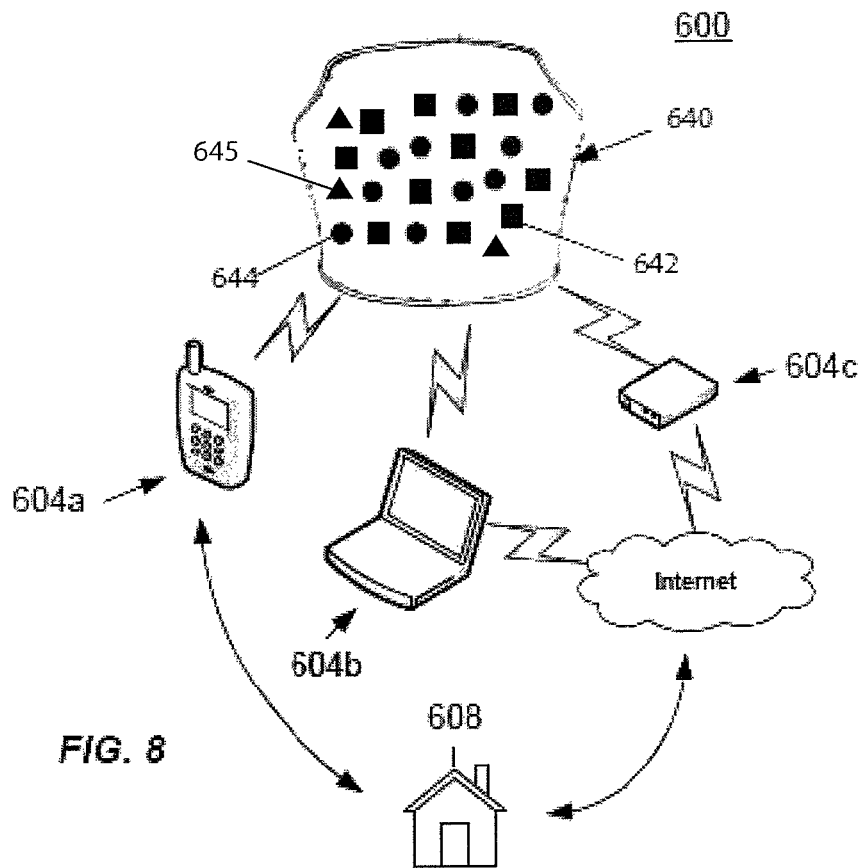
FIG. 8 illustrates an exemplary embodiment of a home usable mapping system capable of recording or communicating with the physician, in accordance with aspects of the present invention.

The one or more electrodes 142 and/or ultrasound elements 144 can be connected to computer 110, such as via a wired and/or wireless connection (see FIG. 8). Computer 110 can control the operation of the one or more electrodes 142 and/or ultrasound elements 144. In some embodiments, computer 110 can shut off selected electrodes 142 and/or ultrasound elements 144, leaving only the associated electrodes 142 and/or ultrasound elements 144 that cover one or more areas of interest being turned on.

System 100 can be used to create a three-dimensional database of dipole densities d(y) and distance measurements at the epicardial surface of the heart. The distance measurements can include, but are not limited to: the distance between at least one of the electrodes 142 and the epicardial surface, the distance between at least one of the electrodes 142 and an ultrasound element 144, and the distance between the epicardial surface and an ultrasound element 144. Knowing the speed of sound in the particular environment, as well as the timing of the delivery of sound waves by the transducer, the distance between an ultrasound transducer, a reflected surface, and an ultrasound sensor can be calculated, as described herein below. Alternatively or additionally, the distance measurements can be calculated by analyzing the received signal amplitude, a shift in frequency between transmitted and received signals, and/or an ultrasound sensor recorded angle. System 100 can also be configured to produce continuous, real time geometries of the tissue of a patient. System 100 can provide one or more of: tissue geometry information such as tissue position, tissue thickness (e.g. cardiac wall thickness) and tissue motion (e.g. cardiac wall motion) information; distance information such as distance between two tissue locations, and distance between a tissue location and a device component location; tissue electrical activity information; status of ablation of a portion of tissue; status of resynchronization pacing, and/or combinations of these.

In some embodiments, the present invention incorporates one or more ultrasound elements 144 comprising both an ultrasound transducer and an ultrasound sensor, each preferably contained in a single component. The ultrasound sensor is configured to record or otherwise detect the wave reflections that result from the ultrasound waves emitted from one or more ultrasound transducers. In addition to determining real-time continuous anatomical geometry information, the detected wave reflections can be used to determine real-time continuous measurements of the position of at least one of the electrodes 142 and/or at least one ultrasound element 144. This information can be used to enhance one or more dipole density d(y) calculations. Measurements can be taken to determine the thickness of an object, such as the thickness of cardiac tissue, which can be used to determine an ablation parameter such as power or time of energy delivery.

In a typical embodiment, an ultrasound element 144 comprising a piezo crystal transmits acoustic waves and receives the reflections of those waves. As is well known to those skilled in the art, the timing between transmitting and receiving can be used to determine the distance between the transmitting and receiving surfaces, and one or more reflective surfaces (e.g. reflective tissue surfaces). In some embodiments, precise distances and dimensions of target cardiac tissue is determined, resulting in a more precise and effective diagnosis and/or therapy.

By having precise anatomical and other distance information, the dipole density calculations will be similarly precise. In some embodiments, one or more ultrasound elements 144 are constructed and arranged to produce sound waves in at least one of either constant or pulsed excitation, such as sounds waves between 3 megahertz and 18 megahertz. The waves emitted by one or more ultrasound elements 144 can be at constant frequency and/or produced by a chirp of changing frequency (to allow pulse compression or demodulation on reception). The precision in dipole density calculations along with the distance measurements will allow for the precise detailing of the electrical activity in the cardiac cells and will allow for the precise identification of which cells are the earliest sites of activation. In some embodiments, one or more ultrasound elements 144 can be configured to automatically detect the distance from one or more ultrasound elements 144 to the epicardial surface via a first reflection and further detect the cardiac wall thickness via a second reflection. In another embodiment, one or more ultrasound elements 144 integrate multiple reflections to construct an anatomical geometry including an epicardial surface of the heart and the thickness of the associated myocardium.

In some embodiments, one or more ultrasound elements 144 include at least one crystal, typically comprised of a piezoelectric material, which is positioned proximate to the center of each electrode 142 within an electrode array. In another embodiment, one or more ultrasound elements 144 include at least one crystal positioned between two or more electrodes 142, such as to create a device with a ratio of mapping electrodes 142 to ultrasound elements 144 of 1:1, 2:1, 5:2, 3:1, 4:1 or another ratio. The at least one crystal can be constructed and arranged to transmit ultrasonic signals and/or to receive ultrasonic signals (e.g. receive ultrasonic signals transmitted by the same or different crystals and/or the reflections of those signals). In another embodiment, one or more ultrasound elements 144 comprise a plurality of crystals, such as a plurality of crystals arranged in an array.

In some embodiments, one or more ultrasound elements 144 comprise a piezoelectric film covering one or more electrodes 142, such as one or more electrodes 142 within an array. In some embodiments, one or more ultrasound elements 144 can be constructed as part of an electrode 142. For example, system 100 can comprise a sensor/electrode combination.

Figure 2:
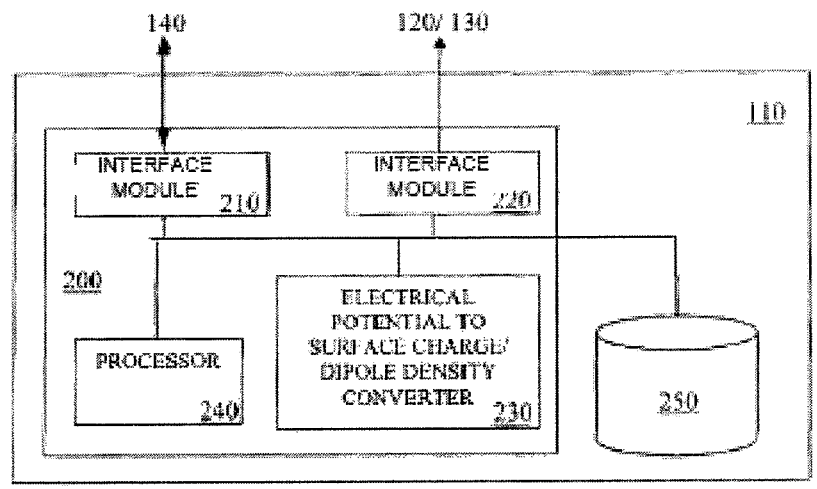
FIG. 2 illustrates a computer architecture forming part of the mapping system of FIG. 1, in accordance with aspects of the present invention.

FIG. 2 provides an example embodiment of a computer architecture 200 that can form part of mapping system 100. Architecture 200 includes interface module 210 for interfacing with the vest 140, interface module 220 for interfacing with output devices 120, 130, and at least one processor 240. The computer 110 includes at least one computer memory 250. The foregoing are generally known, however the present invention further includes an electric-potential to surface-charge-density and/or dipole-density converter module 230. Converter module 230 includes instructions necessary for carrying out the methods described herein, when executed by processor 240, wherein the results of such processing are stored in memory 250, as would be understood by one skilled in the art having the benefit of this disclosure.

In some embodiments, the 3D geometry can be accommodated by integrating anatomical data from CT/MRI scans with the epicardial geometry determined from analysis of the received acoustic signals. The CT/MRI scans can include data to determine torso geometry. The CT/MRI scans can also provide data associated with an epicardial surface surrounding the heart, where those of ordinary skill would understand that the epicardial surface can be used to register the CT/MRI data with data calculated from the devices of the present invention. Further, locating the epicardial surface can include determining or otherwise providing data to be associated with the location of the heart within the torso.

In accordance with some embodiments of the invention, system 100 is configured to generate a table of dipole densities v(P', t) that embody an ionic nature of cellular membranes across the epicardium of a given heart of a patient, comprising:

a) a measuring and recording unit that measures and records electric potential data $V_e$ at given positions P proximate the patient's torso surface, b) an a/d-converter that converts the at least one electric potentials $V_e$ into digital voltage data, c) a processor that transforms the digital voltage data into dipole charge density data, and d) a memory that stores the electric potential data $V_e$ and the transformed cellular membrane dipole density data.

Referring again to FIG. 2, architecture 200 includes a measuring and recording unit, such as interface module 210 which is configured to obtain electric potential data $V_e$ at given positions P proximate the patient's torso surface, the converter module 230 includes an a/d-converter that converts the electric potentials $V_e$ into digital voltage data, the processor 240 transforms the digital voltage data into dipole charge density data, and the memory 250 stores the electric potential data $V_e$ and the transformed cellular membrane dipole density data.

The measuring and recording unit includes multiple electrodes positioned proximate the patient's torso surface. In some embodiments, the system can further include a wearable garment and at least one of the multiple electrodes can be coupled to the wearable garment. In some embodiments, the wearable garment is flexible and conforms closely to the patient's torso surface and can urge one or more electrodes against the torso surface with a consistent position to prevent movement of the one or more electrodes. The wearable garment can be selected from the group consisting of: vest; shirt; bib; arm band; torso band; any patient-attachable assembly capable of maintaining the one or more electrodes in contact with the torso surface or sufficiently close thereto; and/or combinations thereof.

In some embodiments, the processor includes a computer program embodying an algorithm that, when executed, transforms the digital voltage data into cellular membrane dipole density data.

In some embodiments, the system further includes one or more ultrasound transducers positioned proximate the patient's torso surface, the one or more ultrasound transducers being configured to emit waves toward an epicardial surface, and one or more ultrasound sensors positioned proximate the patient's torso surface, the one or more ultrasound sensors being configured to receive reflections of the waves from the epicardial surface, wherein the measuring and recording unit further measures and records the sensor information. In some embodiments, one or more ultrasound transducers are further configured to function as an ultrasound sensor.

In some embodiments, the processor is configured to receive sensor data from the one or more sensors and generate distance measurements from the epicardial surface. The distance measurement can be produced by analyzing at least one of: timing of received signal; recorded signal amplitude; sensor recorded angle; or signal frequency changes In some embodiments, the system includes more than one wearable garment and the multiple electrodes, ultrasound transducers, or ultrasound sensors are coupled to different wearable garments. For example, the multiple electrodes are coupled to a first wearable garment, and the ultrasound transducers and ultrasound sensors are coupled to a second wearable garment. The wearable garments can be selected from the group consisting of: vest; shirt; bib; arm band; torso band; any patient-attachable assembly capable of maintaining the one or more electrodes, one or more ultrasound transducers, and one or more ultrasound sensors in contact with the torso surface, or sufficiently close thereto that a monitorable signal is detectable.

In some embodiments, the system further includes an imaging unit that represents the cellular membrane dipole densities v(P',t) as a two-dimensional image or time-dependent sequence of images.

In some embodiments, the system further includes an imaging unit that represents the cellular membrane dipole densities v(P',t) as a three-dimensional image or time-dependent sequence of images.

Figure 3:
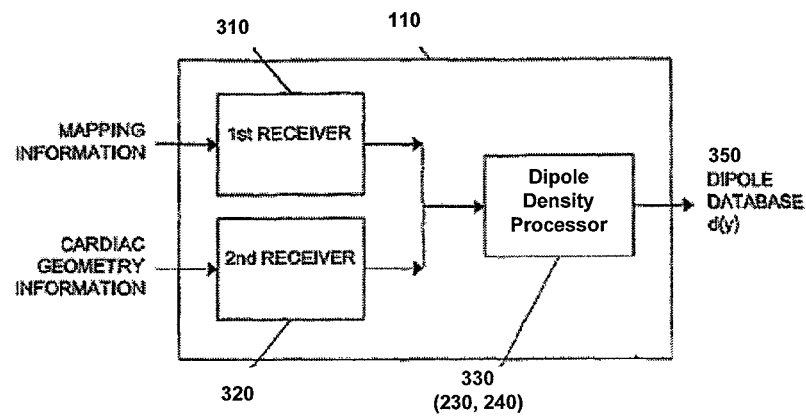
FIG. 3 illustrates a schematic view for determining a database table of dipole densities d(y), in accordance with aspects of the present invention.

FIG. 3 shows a schematic view of some elements of computer 110 used for determining a database table of dipole densities d(y). Computer 110 includes a first receiver 310 configured to receive electrical potentials from the one or more electrodes, such as electrodes 142 of FIG. 1. Computer 110 further includes a second receiver 320 configured to receive cardiac geometry information from an imaging instrument, such as CT; MRI; ultrasound; or a generic model of a heart. This anatomical imaging can be generated in real-time and/or imported from previous imaging from one or more of CT, MRI, ultrasound (internal or external), or other imaging apparatus. Dipole density processor 330 receives electrical information from first receiver 310 and cardiac geometry information from the second receiver 320. Dipole density processor 330, which can comprise converter module 230 and processor 240, includes a mathematical processing element or other electronic module including software and/or hardware for performing mathematical or other calculations. Dipole density processor 330 preferably uses one or more algorithms to process the received electrical and geometry information to produce a database table of dipole densities d(y) 350. Alternatively or additionally, dipole density processor 330 can be configured to produce a database table of surface charge information.

As discussed above, in some embodiments the vest 140 can further include one or more ultrasound transducers and/or one or more ultrasound sensors to provide cardiac geometry information to the second receiver 320. The one or more ultrasound transducers transmit ultrasound waves, such as waves configured to reflect off one or more structures of the heart, and be recorded by the ultrasound sensors (e.g. reflections from the epicardial surface and one or more of the inner surfaces or structures of the heart). Dipole density processor 330 receives electrical information from first receiver 310 and ultrasound cardiac geometry information from the second receiver 320. Dipole density processor 330, which can comprise converter module 230 and processor 240, includes a mathematical processing element or other electronic module including software and/or hardware for performing mathematical or other calculations. Dipole density processor 330 preferably uses one or more algorithms to process the received electrical and geometry information to produce a database table of dipole densities d(y) 350.

The geometric model of the epicardial surface can be processed by the dipole density processor 330 into multiple small triangles (triangularization) and/or other polygonal shapes (e.g., squares, tetrahedral, hexagonal, and others). When the polygons are sufficiently small, the dipole density has a small variation over the polygon. In a preferred embodiment, the number of triangles is determined by dipole density processor 330. With the electrodes positioned by a clinician, such as an electrophysiologist, the potentials at each electrode are recorded. The dipole density processor 330 computes the dipole density at all vertices of the triangles. If the dipole density at a vertex is d(y), the total measured potential V(x) at a location x is the sum over all vertices y of d(y) times a matrix W(x,y). A detailed description is provided in reference to FIG. 4.

In a preferred embodiment, dipole density processor 330 implements a progressive algorithm that can be modified and/or refined in order to improve spatial and/or time resolution of the database of dipole densities that are produced. The dipole densities d(y) can be obtained by solving a linear system of equations. Thereby a map of dipole densities can be created at each corresponding time interval. The synthesis of the maps generates a cascade of the activation sequence of each corresponding heart beat that can be used to diagnose cardiac wall tissue, such as to identify an origin of aberrant electrical activity or otherwise diagnose an arrhythmia. These sequential activation maps of dipole densities and/or other dipole density information as described herein can be used to diagnose and/or treat numerous forms of cardiac disease such as when the dipole density information is used to diagnose and/or treat an arrhythmia, ischemia and/or compromised myocardial function.

The measuring electrodes used in the present invention are placed on or proximate the torso surface. Due to the inhomogeneous structure of the body, it is difficult to localize the actual sources of the skin electrode measured potentials. A highly complicated boundary value problem must be solved with boundary conditions that are poorly known. Prior art attempts at determining the "action potential" from body surface ECG (alone) have not been very successful.

Utilizing the formulas in the '313 patent, '690 publication and '517 publication, the present invention calculates the dipole densities using external electrodes on the vest, in combination with cardiac geometry information from an imaging instrument (such as CT; MRI; ultrasound); or the optional external ultrasound transducers and/or ultrasound sensors on the vest.

Figure 4:
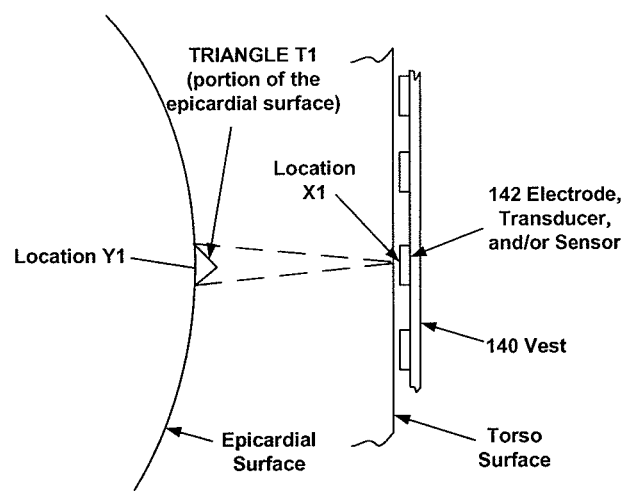
FIG. 4 illustrates a schematic view for determining a database table of dipole densities d(y) using finite elements, in accordance with aspects of the present invention.

Referring now to FIG. 4, an embodiment of a system for determining a database table of dipole densities d(y) of a patient is illustrated. System 100, shown in FIG. 1, is configured to create a database table of three-dimensional dipole densities d(y) based on voltage potentials and image information relating to the heart, as has been described above.

As shown in FIG. 4, triangle T1, defined by system 100 is at location Y1. The contribution of triangle T1 to the potential at location X1 can be computed from the dipole density at the vertices of T1. The dipole density processor 330 determines the desired dipole density d(y) from the total measured potential V(x), which is the sum resulting from all the triangles defined by system 100.

When sufficient potential values V(x) are measured (e.g. from 10 to 10,000 with increasing number of measured potentials providing more accurate results), the dipole density d(y) at many equally distributed vertices y on the epicardial surface is calculated (e.g. from 10 to 50,000 with increasing number of calculated potentials providing more detailed results) by solving a system of linear equations. By interpolation of the measured and/or calculated potentials (e.g. with application of splines) their number can be increased to a higher number of regions. This calculation of dipole density results, such as via an automatic computer program forming at least part of dipole density processor 330.

In some embodiments, the results are presented in a visual, anatomical format, such as depicting the dipole densities on a geometric model of the epicardial surface in relation to time (t). This format allows a clinician, such as an electrophysiologist, to determine the activation sequence, or other electrical and mechanical measures, on the epicardial surface, such as to determine treatment locations for a cardiac arrhythmia or other inadequacy in cardiac tissue health, such as force of tissue contraction and motion of the epicardial surface. The results can be shown on a display unit 120, or on a separate display not shown, such as a color display. In some embodiments, the device of the present invention is implemented as, or includes, a software program that is executable by at least one processor. The software program can be integrated into one or more of: an ECG system; a cardiac tissue ablation system; an imaging system; a computer; and combinations of these.

Figure 5:
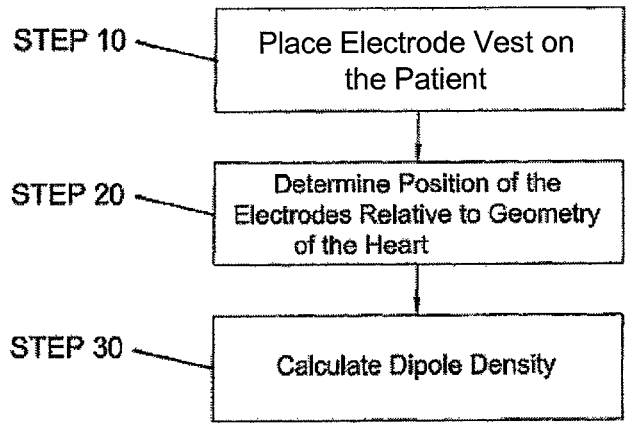
FIG. 5 illustrates a flow chart of a method for determining a database table of dipole densities, in accordance with aspects of the present invention.

FIG. 5 illustrates one embodiment of a method for determining a database table of dipole densities d(y) of the epicardial surface of a patient's heart. In Step 10, a vest having an array of one or more electrodes (e.g. vest 140 of system 100 of FIG. 1) is placed on the torso of the patient. In Step 20, the geometry of the epicardial surface can be obtained in relation to the positions of the one or more electrodes disposed within the electrode array. In addition to the epicardial surface geometry, the magnitude and other properties of motion of cardiac wall tissue can be determined. In addition, the thickness of a patient's heart tissue can be determined. This information will enable a clinician to determine what treatment, (e.g., what ablation parameters) can be appropriate for the patient. One or more ultrasound transducers and sensors can be utilized in this step, as discussed above. Alternatively or additionally, the geometry of the epicardial surface is obtained in relation to the electrode array position, such as by importing a geometry model from an imaging study (e.g., using computed tomography, MRI and/or ultrasound). The surface of the geometry of the corresponding epicardial surface is generally divided into small polygons, such as in the form of at least 1000 triangles of similar size.

In Step 30, the dipole density d(y) can be calculated at each vertex y from the measured potential values x. The measurements can be repeated successively during the cardiac cycle, such as once each millisecond, giving the electrophysiologist a dynamic progression of the activation sequence. The information of the time dependent dipole densities can be depicted as an animated color map of activation for each heart beat across the epicardial surface. The information can be used to diagnose and/or treat a patient with a cardiac arrhythmia, such as atrial fibrillation, or an inadequately synchronized activation sequence, such as in heart failure. Other information obtained can include precise location of foci, conduction-gaps, and/or position of conduction channels.

The dipole density information can be used to determine cardiac tissue treatment locations for lesion creation, such as a lesion created by a catheter-based ablation system. Alternatively, the lesion can be created by an RF, ultrasound, microwave, laser and/or cryogenic energy ablation catheter. The information can also be used to determine the location of pacing electrodes for cardiac resynchronization therapy.

In some embodiments, ablating the cardiac tissue can be based upon the tissue diagnosis. For example, the anatomical information comprising tissue thickness information and at least one of the magnitude of ablation energy or the time period in which ablation energy is delivered, is adjusted based on the tissue thickness information recorded by one or more ultrasound sensors.

Figure 6:
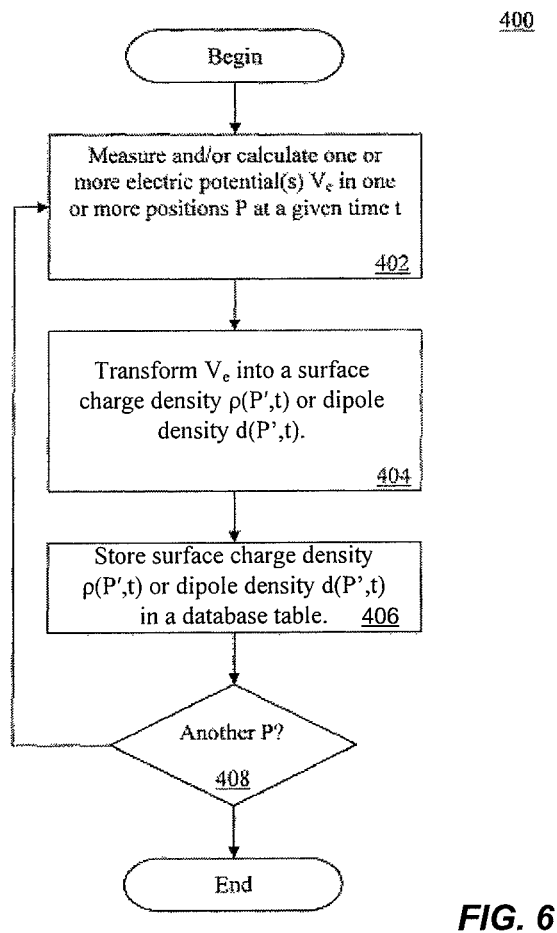
FIG. 6 is an example embodiment of a method of determining and storing dipole densities, in accordance with aspects of the present invention.

FIG. 6 summarizes one method 400 for determining and storing surface charge densities and/or dipole densities in accordance with aspects of the present invention, which have been described in detail above.

In Step 402, mapping system 100 is used to measure and/or calculate one or more electric potential(s) $V_e$ in one or more position(s) P at a given time t. In Step 404, $V_e$ is transformed into a surface charge density ρ(P',t) and/or dipole density d(P',t) In Step 406, the surface charge density ρ(P',t) and/or dipole density d(P',t) is stored in a database table. The method is repeated if there is another P, in Step 408.

Figure 7:
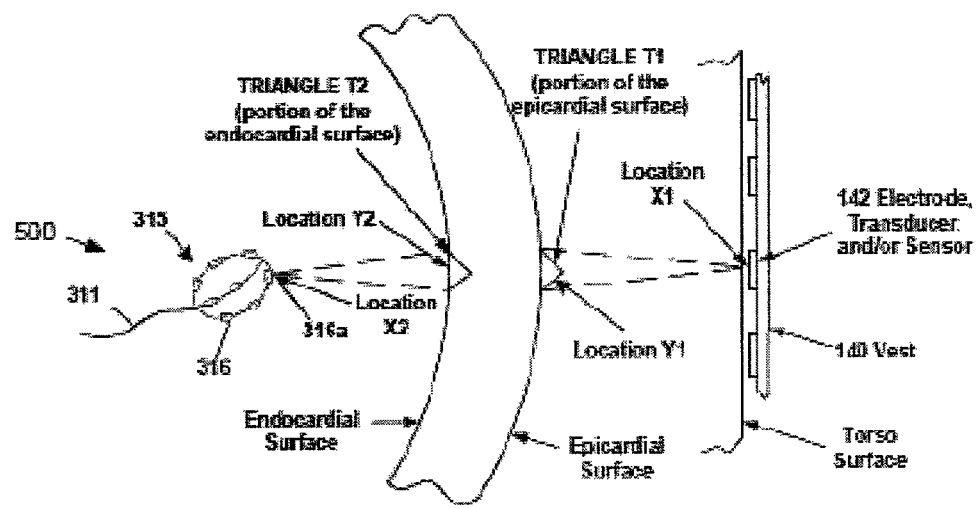
FIG. 7 illustrates a schematic view combining both external and internal systems for determining dipole densities d(y) using finite elements, in accordance with aspects of the present invention.

FIG. 7 shows an embodiment using both external sensor systems and internal sensor systems together. For example, the present systems and methods disclosed above for external sensor-based imaging of the heart can be combined with the devices, systems, and methods using internal sensor-based imaging of the heart disclosed in the '313 patent, '690 publication and '517 publication. FIG. 7 shows the present vest system in combination with system 500, described in detail in the '690 publication and '517 publication, each of which is hereby incorporated by reference. This combination of internal and external electrodes can be used to augment accuracy, specificity, etc., and combining heart chamber geometry with internal and external sensor (voltage) readings can provide simultaneous maps of the epicardium and endocardium walls.

System 500 includes a mapping catheter with a shaft 311, which is inserted into a chamber of a patient's heart, such as the Left Atrium (LA). At the distal end of shaft 311 is an electrode array 315 including multiple electrodes 316. Electrode array 315 is shown in a basket construction, but numerous other constructions can be used including multiple independent arms, spiral arrays, electrode covered balloons, and other constructions configured to place multiple electrodes into a three-dimensional space. Any catheter with one or more electrodes can be used to supply mapping information to system 100, which is configured to create a database table of three-dimensional dipole densities d(y) based on voltage potentials and image information relating to the heart, as has been described above.

As shown in FIG. 7, triangle T2, is at location Y2 on the endocardial surface and electrode 316a is at location X2. The contribution of triangle T2 to the potential at location X2 can be computed from the dipole density at the vertices of T1. The dipole density processor 330 determines the desired dipole density d(y) from the total measured potential V(x), which is the sum resulting from all the triangles defined by system 100.

When sufficient potential values V(x) are measured (e.g. from 10 to 50,000) with increasing number of measured potentials providing more accurate results, the dipole density d(y) at many equally distributed vertices y on the endocardial surface can be calculated (e.g. from 10 to 50,000 with increasing number of calculated potentials providing more detailed results) by solving a system of linear equations. By interpolation of the measured and/or calculated potentials (e.g. with application of splines) their number can be increased to a higher number of regions.

In some embodiments, the results are presented in a visual, anatomical format, such as on a display depicting the dipole densities on a geometric model of the endocardial surface and epicardial surface in relation to time (t). This format allows a clinician, such as an electrophysiologist, to determine the activation sequence, or other electrical and mechanical measures, on the endocardial surface and/or epicardial surface, such as to determine treatment locations for a cardiac arrhythmia or other inadequacy in cardiac tissue health, such as force of tissue contraction and motion of an endocardial surface and/or an epicardial surface. The results can be shown on a display unit 120, or on a separate display not shown, such as a color display.

FIG. 8 shows embodiments for a mapping system 600 for monitoring of a patient at their home or otherwise remote from a clinical setting. The system 600 can use many of the elements and methods described above for determination of dipole densities. The system 600 includes a vest 640, which can use the same or similar features as vest 140 described above, and a recording device 604a, computer 604b and/or communication system 604c.

Vest 640 can include one or more electrodes 642. In some embodiments, vest 640 can further include one or more ultrasound elements 644, such as one or more ultrasound transducers and/or ultrasound sensors. Vest 640 can be flexible and conform closely to the body of the patient and can be made of any suitable materials. Vest 640 can be configured so that the one or more electrodes 642 and/or ultrasound elements 644 are urged against the torso surface or skin at a consistent position, such as to prevent movement of the element across the skin. In some embodiments, the one or more electrodes 642 and/or ultrasound elements 644 can be positioned on both the front and the back of the patient. In other embodiments, the one or more electrodes 642 and/or ultrasound elements 644 can be positioned on only the front or back of the patient, depending on application. Alternatively, the one or more electrodes 642 and/or ultrasound elements 644 can be attached directly to the skin. While the description discloses one or more electrodes 642 and/or one or more ultrasound elements 644 used with the vest, garment, or direct skin attachment, the invention also envisions embodiments that only include electrodes 642 or only ultrasound elements 644.

In some embodiments, vest 640 or another component of system 600 includes one or more additional sensors or transducers, functional element 645. Functional elements 645 can comprise an element selected from the group consisting of: a pressure sensor such as a blood pressure sensor; a pH sensor; a glucose sensor; a respiration sensor; a salinity or other sweat level sensor; an EEG sensor such as an EEG sensor placed on the scalp of the patient; an oxygen level sensor such as an oxygen level sensor placed on the finger of the patient; an eye gaze sensor; and combinations of these.

The one or more electrodes 642, ultrasound elements 644, and/or functional elements 645 can be coupled to the recording device 604a, computer 604b and/or communication system 604c, with either a wired (not shown) or wireless connection (e.g., Bluetooth, Wi-Fi, or other wireless means). The recording device 604a, computer 604b and/or communication system 604c can control the operation of the one or more electrodes 642, ultrasound elements 644, and/or functional elements 645. This control feature can be programmed into their systems or can be done remotely via a remote connection (e.g., from a physician's office 608). In some embodiments, the recording device 604a, computer 604b and/or communication system 604c can turn on or shut off selected electrodes 642, ultrasound elements 644, and/or functional elements 645, leaving only the associated electrodes 642, ultrasound elements 644, and/or functional elements 645 that cover one or more areas of interest being turned on.

In some embodiments, the recording device 604a can be a portable device for monitoring and recording various electrical and/or other signal activities of the one or more electrodes 642, ultrasound elements 644, and/or functional elements 645, similar to a Holter or other mobile-patient monitor. The recording device 604a can be configured to continuously monitor and record, or only record on an as needed basis when a recordable event happens. Once the data is recorded, the recording device 604a can be transmitted to the physician's office to be analyzed. In other embodiments, the recording device 604a can be a smart phone, such as a Galaxy S4, having an application for recording the signal activities. Once recorded, the smart phone can also be capable of transmitting the information, for example, to the physician's office.

In some embodiments, the computer 604b can have the capability of continuously monitoring various signal activities of the one or more electrodes 642, ultrasound elements 644, and/or functional elements 645. The computer 604b can also have the capability of analyzing the data from the one or more electrodes 642, ultrasound elements 644, and/or functional elements 645, similar to system 100 described above. In some embodiments, computer 604b comprises one or more algorithms constructed and arranged to analyze one or more of: cardiac geometry; cardiac electrical activity; blood pressure; pH; glucose; respiration; sweat level; brain activity; or blood oxygen level. In some embodiments, computer 604b analyzes cardiac electrical activity and at least one physiologic parameter selected from the group consisting of: blood pressure; pH; glucose; respiration; sweat level; brain activity; or blood oxygen level. The computer 604b can save the monitored or analyzed data in memory, such as on memory card or flash device card or copy it to a disk. The computer 604b can further have the capability of transmitting the analyzed data, for example, to the physician's office, giving the physician real-time feedback as to the health and condition of their patient.

In some embodiments, communication system 604c can include a means of communicating with the physician's office on a real-time basis for remote medical patient monitoring, such as over the internet or other direct communication means (e.g., smart phone). In this way, the physician can monitor the patient 24 hours a day and/or at any time. The system can further include two way communications such that the physician can view the data in real-time while speaking with the patient. The physician can also turn on or shut off selected electrodes 642, ultrasound elements 644 and/or functional elements 645, leaving only the associated electrodes 642, ultrasound elements 644 and/or functional elements 645 that cover one or more areas of interest being turned on.

Other embodiments of the invention will be apparent to those skilled in the art from consideration of the specification and practice of the embodiments disclosed herein. It is intended that the specification and examples be considered as exemplary only, with a true scope and spirit of the invention being indicated by the following claims. In addition, where this application has listed the steps of a method or procedure in a specific order, it can be possible, or even expedient in certain circumstances, to change the order in which some steps are performed, and it is intended that the particular steps of the method or procedure claims set forth herein below not be construed as being order-specific unless such order specificity is expressly stated in the claim.

We claim:

1. A device that generates a table of dipole density data that embody an ionic nature of cellular membranes across the epicardium of a patient's heart, comprising:
    a measuring and recording unit that measures and records electric potential data $V_e$ at given positions P, comprising:
        one or more ultrasound transducers configured to be positioned proximate the patient's torso surface, the one or more ultrasound transducers being configured to emit ultrasound waves toward an epicardial surface of the patient's heart;
        one or more ultrasound sensors configured to be positioned proximate the patients torso surface, the one or more ultrasound sensors being configured to receive reflections of the ultrasound waves from the epicardial surface and to produce sensor data related to the reflected ultrasound waves;
        an array of multiple electrodes configured to be positioned proximate the patient's torso surface;
        at least one probe electrode configured to be positioned within a chamber of the patient's heart; and
        a flexible wearable garment comprising a plurality of electrodes from the multiple electrodes, at least one of the one or more ultrasound transducers, and at least one of the one or more ultrasound sensors, wherein the plurality of electrodes is fixedly mounted within or on the wearable garment such that distances between fixedly mounted electrodes are known separation distances;
    an a/d-converter that converts the electric potential data $V_e$ into digital voltage data;
    a processor configured to transform cardiac surface geometry information from the sensor data related to the reflected ultrasound waves and the digital voltage data into dipole density data; and
    a memory that stores the electric potential data $V_e$ and the dipole density data,
    wherein the processor is configured to:
        record electric signals between electrodes having the known separation distances from the plurality of electrodes to determine calibrated signals values and to determine distances between electrodes for which separation distance is not known based on the electrical signals and the calibrated signal values, the known distance and/or determined distances between electrodes employed to compute the dipole density data at vertices of polygonal shaped projections onto the epicardial surface;
        use the sensor data related to the reflected ultrasound waves to determine real-time continuous anatomical geometry information of the chamber and to determine real-time continuous measurements of the position of at least one of the electrodes, at least one of the ultrasound transducers, and/or at least one of the ultrasound sensors; and
        enhance the dipole density data using at least one of the real-time continuous anatomical geometry information or real-time continuous measurements of the position.

2. The device of claim 1, wherein the wearable garment is flexible and configured to conform closely to the patient's torso surface.

3. The device of claim 1, wherein the wearable garment is configured to urge at least one of the plurality of electrodes, the at least one of the one or more ultrasound transducers, and/or the at least one of the one or more ultrasound sensors of the wearable garment against the patient's torso surface with a consistent position to prevent movement.

4. The device of claim 1, wherein the processor includes a computer program embodying an algorithm that, when executed by a processor, transforms the digital voltage data into dipole density data.

5. The device of claim 1, wherein the processor is configured to receive the sensor data from the one or more sensors and generate distance measurements from the epicardial surface.

6. The device of claim 5, wherein the processor is configured to produce the distance measurements by analyzing at least one of: timing of received signal; recorded signal amplitude; sensor recorded angle; or signal frequency changes.

7. The device of claim 1, wherein the wearable garment is selected from the group consisting of: a vest; a shirt; a bib; an arm band; a torso band; any patient-attachable assembly capable of maintaining the at least one of the multiple electrodes, the at least one of the one or more ultrasound transducers, and/or the at least one of the one or more ultrasound sensors of the wearable garment in contact with the torso surface, or sufficiently close thereto that a monitorable signal is detectable; and/or combinations thereof.

8. The device of claim 1, wherein the device is configured to diagnose at least one of: an arrhythmia; ischemia; or compromised myocardial function.

9. The device of claim 1, wherein the device is configured to treat at least one of: an arrhythmia; ischemia; or compromised myocardial function.

10. A device for creating a database of dipole densities d(y) and distance measurements at an epicardial surface of a patient's heart, the device comprising:
    an array of multiple electrodes configured to be positioned proximate the patients torso surface and a probe electrode configured to be positioned within a chamber of the patient's heart;

one or more ultrasound transducers configured to be positioned proximate the patient's torso surface, the one or more ultrasound transducers being configured to emit ultrasound waves toward the epicardial surface;

one or more ultrasound sensors configured to be positioned proximate the patients torso surface, the one or more ultrasound sensors being configured to receive reflections of the ultrasound waves from the epicardial surface;

a wearable garment comprising a plurality of electrodes from the multiple electrodes, at least one of the one or more ultrasound transducers, and at least one of the one or more ultrasound sensors, wherein distances between electrodes of the wearable garment are known separation distances; and a computer coupled to the multiple electrodes, the one or more ultrasound transducers, and the one or more ultrasound sensors, wherein the computer is configured to:

record electric signals between electrodes having the known separation distances of the wearable garment to determine calibrated signals values and to determine distance measurements between the electrodes for which separation distance is not known based on the electrical signals and the calibrated signal values, and receive mapping information from the multiple electrodes and sensor data from the one or more ultrasound sensors, the sensor data providing cardiac surface geometry information, use the sensor data to determine real-time continuous anatomical geometry information of the chamber and to determine real-time continuous measurements of the position of at least one of the electrodes, at least one of the ultrasound transducers, and/or at least one of the ultrasound sensors; and generate the database of dipole densities d(y) from the distance measurements, the mapping information, and the cardiac surface geometry information, wherein the distance measurements include at least one of the known distances, the determined distances, or real-time continuous measurements of the position, and wherein the cardiac surface geometry includes the real-time continuous anatomical geometry information.

11. The device of claim 10, wherein the wearable garment is flexible and configured to conform closely to the patient's torso surface.

12. The device of claim 10, wherein the wearable garment is flexible and configured to urge at least one of the plurality of electrodes, the at least one of the one or more ultrasound sensors, and/or the at least one of the one or more ultrasound transducers of the wearable garment against the patient's torso surface with a consistent position to prevent movement.

13. The device of claim 10, wherein the wearable garment is selected from the group consisting of: vest; shirt; bib; arm band; torso band; any patient-attachable assembly capable of maintaining the at least one of the multiple electrodes, the at least one of the one or more ultrasound transducers, and/or the at least one of the one or more ultrasound sensors of the wearable garment in contact with the torso surface, or sufficiently close thereto that a monitorable signal is detectable; and/or combinations thereof.

14. The device of claim 10, wherein the computer is coupled to the wearable garment.

15. The device of claim 10, wherein the computer includes:

a dipole density module configured to generate a three dimensional database of dipole densities d(y), wherein the dipole density module is configured to determine a dipole density for polygonal shaped projections onto the epicardial surface and compute the dipole density at all vertices of the polygonal shaped projections.

16. The device of claim 15, wherein the dipole density module generates the database of dipole densities d(y) using a finite elements method.

17. The device of claim 15, wherein the polygonal shaped projections are substantially the same size.

18. The device of claim 15, wherein the dipole density is determined by a number of polygonal shaped projections, the number determined by the size of an epicardial surface.

19. The device of claim 10, wherein the device is configured to provide epicardial surface motion information of the heart.

20. The device of claim 19, wherein the device is configured to provide tissue diagnostic information by analysing both motion information and cell electrical signals.

21. The device of claim 20, wherein the cell electrical signals are recorded by the multiple electrodes.

22. The device of claim 10, wherein the device further includes a display coupled to the computer and configured to display real time motion.

23. The device of claim 10, wherein the computer is configured to produce a geometrical depiction of the heart.

24. The device of claim 10, wherein the device is further configured to determine properties of the cardiac wall.

25. The device of claim 24, wherein the properties include cardiac wall thickness information.

26. The device of claim 24, wherein the properties include precise foci, conduction-gaps, and/or conduction channels position information.

27. The device of claim 10, wherein the distance measurement comprises the distance between at least one of the multiple electrodes and at least one epicardial surface.

28. The device of claim 27, wherein the device is configured to produce the distance measurement by analyzing at least one of: timing of received signal; recorded signal amplitude; sensor recorded angle; or signal frequency changes.

29. The device of claim 10, wherein the device is configured to provide epicardial surface information during a cardiac ablation procedure.

30. The device of claim 29, wherein the ablation procedure comprises delivery of RF, ultrasound, microwave, cryogenic and/or laser energy to tissue.

31. The device of claim 10, wherein at least one of the sensors and at least one of the transducers comprises a single component.

32. The device of claim 10, wherein the computer is configured to determine a map of dipole densities d(y) at corresponding time intervals.

33. The device of claim 10, wherein the computer is configured to generate a synthesis of maps that represents a cascade of activation sequences of each corresponding heart beat from a series of heart beats.

34. The device of claim 10, wherein the device is configured to diagnose at least one of: an arrhythmia; ischemia; or compromised myocardial function.

35. The device of claim 10, wherein the device is configured to treat at least one of: an arrhythmia; ischemia; or compromised myocardial function.

36. A method of processing cardiac activity of a patient, said method comprising:
- placing an array of multiple electrodes, one or more ultrasound transducers, and one or more ultrasound sensors proximate the patients torso surface, including:
  - providing a wearable garment comprising a plurality of electrodes from the multiple electrodes, at least one of the one or more ultrasound transducers, and at least one of the one or more ultrasound sensors, wherein distances between electrodes of the wearable garment are known separation distances;
- calculating dipole densities $d(y)$ by:
  - recording electric signals between electrodes of the wearable garment having known separation distances and determining therefrom calibrated signal values, and calculating distance information, including determining distances between electrodes for which separation distance is not known based on the electrical signals and the calibrated signal values;
  - receiving mapping information from the multiple electrodes;
  - emitting waves toward the epicardial surface with the one or more ultrasound transducers;
  - receiving reflections of the waves from the epicardial surface with the one or more ultrasound sensors to produce sensor data;
  - producing a geometrical depiction of the epicardial surface from the sensor data, including using the sensor data to determine real-time continuous anatomical geometry information of the chamber;
  - using the sensor data to determine real-time continuous measurements of the position of at least one of the electrodes, at least one of the ultrasound transducers, and/or at least one of the ultrasound sensors;
  - receiving mapping information from at least one probe electrode positioned within a chamber of the patient's heart; and
  - generating a database of dipole densities $d(y)$ with a dipole density module, wherein the dipole density module determines dipole densities $d(y)$ of polygonal shaped projections onto the geometrical depiction of the epicardial surface, wherein the dipole density module computes the dipole density at all vertices of the polygonal shaped projections from the mapping information and the distance information; and
  - calculating distances to the epicardial surface or movement of the epicardial surface by analysing signals received from the one or more ultrasound sensors.

37. The method of claim 36, wherein the dipole density module generates the database of dipole densities $d(y)$ using a finite elements method.

38. The method of claim 36, wherein the wearable garment is configured to urge the at least one of the multiple electrodes, the at least one of the one or more ultrasound sensors and/or the at least one of the one or more ultrasound transducers of the wearable garment against the torso surface with a consistent position to prevent movement.

39. The method of claim 36, wherein the wearable garment is selected from the group consisting of: vest; shirt; bib; arm band; torso band; any patient-attachable assembly capable of maintaining the at least one of the multiple electrodes in contact with the torso surface or sufficiently close thereto that a monitorable signal is detectable; and/or combinations thereof.

40. The method of claim 36, wherein calculating the distances to the epicardial surface further comprises calculating tissue thickness information.

41. The method of claim 36, including using the dipole densities $d(y)$ to locate an origin of abnormal electrical activity of a heart.

42. The method of claim 36, including using the dipole densities $d(y)$ to diagnose at least one of: an arrhythmia; ischemia; or compromised myocardial function.

43. The method of claim 36, including using the dipole densities $d(y)$ to treat at least one of: an arrhythmia; ischemia; or compromised myocardial function.

44. The method of claim 36, wherein calculating the dipole densities $d(y)$ includes a processor executing a computer program stored in a memory, the computer program embodying an algorithm for generating a table of dipole densities in the memory.

45. The method of claim 36, wherein at least one ultrasound transducer comprises at least one ultrasound sensor.

* * * * *